United States Patent
Beardsley et al.

(10) Patent No.: US 8,403,196 B2
(45) Date of Patent: Mar. 26, 2013

(54) DISSECTION TIP AND INTRODUCER FOR SURGICAL INSTRUMENT

(75) Inventors: John W. Beardsley, Wallingford, CT (US); Stanislaw Kostrzewski, Newtown, CT (US); Frank C. Maffei, Shelton, CT (US); Lee Ann Olson, Wallingford, CT (US); Sachin Shah, Milford, CT (US); William R. Mayfield, Whitehall, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/371,799

(22) Filed: Feb. 13, 2012

(65) Prior Publication Data

US 2012/0143218 A1   Jun. 7, 2012

Related U.S. Application Data

(60) Division of application No. 13/371,643, filed on Feb. 13, 2012, which is a division of application No. 12/571,659, filed on Oct. 1, 2009, now Pat. No. 8,136,711, which is a continuation-in-part of application No. 11/851,495, filed on Sep. 7, 2007, now abandoned.

(60) Provisional application No. 60/843,254, filed on Sep. 8, 2006.

(51) Int. Cl.
*A61B 17/068* (2006.01)
(52) U.S. Cl. ............... 227/175.1; 227/19; 227/176.1; 606/139; 606/219
(58) Field of Classification Search .......... 227/19, 227/175.1, 176.1, 180.1, 156; 606/139, 219, 606/191, 207, 148, 151, 41
See application file for complete search history.

(56) References Cited

U.S. PATENT DOCUMENTS

| | | |
|---|---|---|
| 2,887,111 A | 5/1959 | Diaz |
| 4,545,373 A | 10/1985 | Christoudias |
| 4,576,164 A | 3/1986 | Richeson |
| 4,601,710 A | 7/1986 | Moll |
| 4,723,545 A | 2/1988 | Nixon et al. |
| 4,873,977 A | 10/1989 | Avant et al. |
| 5,047,039 A | 9/1991 | Avant et al. |
| 5,129,570 A | 7/1992 | Schulze et al. |
| 5,217,460 A | 6/1993 | Knoepfler |
| 5,234,454 A | 8/1993 | Bangs |
| 5,281,236 A | 1/1994 | Bagnato et al. |
| 5,282,807 A | 2/1994 | Knoepfler |
| 5,350,104 A | 9/1994 | Main et al. |
| 5,355,897 A | 10/1994 | Pietrafitta et al. |
| 5,360,154 A | 11/1994 | Green |
| 5,376,376 A | 12/1994 | Li |
| 5,397,324 A | 3/1995 | Carroll et al. |

(Continued)

FOREIGN PATENT DOCUMENTS

| | | |
|---|---|---|
| WO | WO 01/21060 A1 | 3/2001 |
| WO | WO 02/00121 A1 | 1/2002 |

(Continued)

OTHER PUBLICATIONS

European Search Report for EP 10251721.6-2310 date of completion is Feb. 18, 2011 (3 pages).

*Primary Examiner* — Scott A. Smith
(74) *Attorney, Agent, or Firm* — Covidien LP

(57) ABSTRACT

The present disclosure describes a surgical fastener applying apparatus that includes an elongate body portion having proximal and distal ends, an end effector including a first movably coupled to a second jaw that is positioned at the distal end of the elongate body portion, and an introducer member. The introducer member has proximal and distal portions, and is configured and dimensioned for releasable connection with the end effector. The introducer member is at least partially formed from a flexible material, and is configured and dimensioned to separate target tissue from collateral tissue prior to positioning of the target tissue between the first and second jaws of the end effector.

14 Claims, 29 Drawing Sheets

U.S. PATENT DOCUMENTS

| | | | |
|---|---|---|---|
| 5,425,745 A | 6/1995 | Green et al. | |
| 5,445,644 A | 8/1995 | Pietrafitta et al. | |
| 5,467,911 A | 11/1995 | Tsuruta et al. | |
| 5,487,500 A | 1/1996 | Knodel et al. | |
| 5,501,654 A | 3/1996 | Failla et al. | |
| 5,507,754 A | 4/1996 | Green et al. | |
| 5,522,788 A | 6/1996 | Kuzmak | |
| 5,527,298 A | 6/1996 | Vance et al. | |
| 5,531,744 A | 7/1996 | Nardella et al. | |
| 5,562,241 A | 10/1996 | Knodel et al. | |
| 5,597,107 A | 1/1997 | Knodel et al. | |
| 5,603,698 A | 2/1997 | Roberts et al. | |
| 5,632,432 A | 5/1997 | Schulze et al. | |
| 5,662,258 A | 9/1997 | Knodel et al. | |
| 5,665,100 A | 9/1997 | Yoon | |
| 5,690,653 A | 11/1997 | Richardson et al. | |
| 5,766,187 A | 6/1998 | Sugarbaker | |
| 5,772,099 A | 6/1998 | Gravener | |
| 5,810,855 A | 9/1998 | Rayburn et al. | |
| 5,816,471 A | 10/1998 | Plyley et al. | |
| 5,902,333 A | 5/1999 | Roberts et al. | |
| 5,908,427 A | 6/1999 | McKean et al. | |
| 5,984,964 A | 11/1999 | Roberts et al. | |
| 6,032,849 A | 3/2000 | Mastri et al. | |
| 6,099,537 A | 8/2000 | Sugai et al. | |
| 6,099,551 A | 8/2000 | Gabbay | |
| 6,117,148 A | 9/2000 | Ravo et al. | |
| 6,149,660 A | 11/2000 | Laufer et al. | |
| 6,165,183 A | 12/2000 | Kuehn et al. | |
| 6,193,129 B1 | 2/2001 | Bittner et al. | |
| 6,443,970 B1 | 9/2002 | Schulze et al. | |
| 6,458,128 B1 | 10/2002 | Schulze | |
| 6,464,702 B2 | 10/2002 | Schulze et al. | |
| 6,506,210 B1 | 1/2003 | Kanner | |
| 6,530,942 B2 | 3/2003 | Fogarty et al. | |
| 6,554,829 B2 | 4/2003 | Schulze et al. | |
| 6,582,452 B2 | 6/2003 | Coleman et al. | |
| 6,592,581 B2 | 7/2003 | Bowe | |
| 6,616,661 B2 | 9/2003 | Wellman et al. | |
| 6,616,686 B2 | 9/2003 | Coleman et al. | |
| 6,620,161 B2 | 9/2003 | Schulze et al. | |
| 6,623,482 B2 | 9/2003 | Pendekanti et al. | |
| 6,648,900 B2 | 11/2003 | Fleischman et al. | |
| 6,648,901 B2 | 11/2003 | Fleischman et al. | |
| 6,652,521 B2 | 11/2003 | Schulze | |
| 6,656,193 B2 | 12/2003 | Grant et al. | |
| 6,673,084 B1 | 1/2004 | Peterson et al. | |
| 6,685,712 B2 | 2/2004 | Cummins et al. | |
| 6,695,840 B2 | 2/2004 | Schulze et al. | |
| 6,702,828 B2 | 3/2004 | Whayne | |
| 6,767,356 B2 | 7/2004 | Kanner et al. | |
| 6,773,435 B2 | 8/2004 | Schulze et al. | |
| 6,773,439 B2 | 8/2004 | George et al. | |
| 6,773,444 B2 | 8/2004 | Messerly | |
| 6,790,217 B2 | 9/2004 | Schulze et al. | |
| 6,821,273 B2 | 11/2004 | Mollenauer | |
| 6,905,057 B2 | 6/2005 | Swayze et al. | |
| 6,926,731 B2 | 8/2005 | Coleman et al. | |
| 6,939,328 B2 | 9/2005 | Raulerson | |
| 6,951,568 B1 | 10/2005 | Chin | |
| 6,976,969 B2 | 12/2005 | Messerly | |
| 7,041,099 B2 | 5/2006 | Thomas et al. | |
| 7,063,699 B2 | 6/2006 | Hess et al. | |
| 7,090,686 B2 | 8/2006 | Nobles et al. | |
| 7,128,748 B2 | 10/2006 | Mooradian et al. | |
| 7,147,138 B2 | 12/2006 | Shelton, IV | |
| 7,300,444 B1 | 11/2007 | Nielsen et al. | |
| 7,364,060 B2 | 4/2008 | Milliman | |
| 7,396,356 B2 | 7/2008 | Mollenauer | |
| 7,402,172 B2 | 7/2008 | Chin et al. | |
| 7,404,508 B2 | 7/2008 | Smith et al. | |
| 7,419,080 B2 | 9/2008 | Smith et al. | |
| 7,500,979 B2 | 3/2009 | Hueil et al. | |
| 7,556,186 B2 | 7/2009 | Milliman | |
| 7,857,187 B2 | 12/2010 | Milliman | |
| 7,866,523 B1 | 1/2011 | White et al. | |
| 8,066,166 B2 * | 11/2011 | Demmy et al. | 227/175.1 |
| 8,136,711 B2 * | 3/2012 | Beardsley et al. | 227/175.1 |
| 2002/0069884 A1 | 6/2002 | Boyd et al. | |
| 2002/0074004 A1 | 6/2002 | Boyd et al. | |
| 2002/0173809 A1 | 11/2002 | Fleischman et al. | |
| 2003/0028178 A1 | 2/2003 | Chin | |
| 2003/0144686 A1 | 7/2003 | Martinez et al. | |
| 2004/0068278 A1 | 4/2004 | Fleischman et al. | |
| 2004/0236326 A1 | 11/2004 | Schulze et al. | |
| 2004/0243151 A1 | 12/2004 | Demmy et al. | |
| 2005/0022601 A1 | 2/2005 | Blakley | |
| 2005/0059996 A1 | 3/2005 | Bauman et al. | |
| 2005/0080434 A1 | 4/2005 | Chung et al. | |
| 2005/0096670 A1 | 5/2005 | Wellman et al. | |
| 2005/0096671 A1 | 5/2005 | Wellman et al. | |
| 2005/0119669 A1 | 6/2005 | Demmy | |
| 2005/0143756 A1 | 6/2005 | Jankowski | |
| 2005/0216055 A1 | 9/2005 | Scirica et al. | |
| 2005/0216057 A1 | 9/2005 | Coleman et al. | |
| 2005/0228413 A1 | 10/2005 | Binmoeller et al. | |
| 2005/0228446 A1 | 10/2005 | Mooradian et al. | |
| 2006/0030877 A1 | 2/2006 | Martinez et al. | |
| 2006/0129165 A1 | 6/2006 | Edoga et al. | |
| 2006/0151568 A1 | 7/2006 | Weller et al. | |
| 2006/0208028 A1 | 9/2006 | Kanner | |
| 2006/0229643 A1 | 10/2006 | Nolan et al. | |
| 2006/0264986 A1 | 11/2006 | Park et al. | |
| 2007/0005084 A1 | 1/2007 | Clague et al. | |
| 2007/0021840 A1 | 1/2007 | Lopera | |
| 2007/0149993 A1 | 6/2007 | Kasahara et al. | |
| 2007/0187455 A1 | 8/2007 | Demmy et al. | |
| 2007/0221700 A1 | 9/2007 | Ortiz et al. | |
| 2007/0221701 A1 | 9/2007 | Ortiz et al. | |
| 2008/0249565 A1 | 10/2008 | Michler et al. | |
| 2008/0269793 A1 | 10/2008 | Scirica et al. | |
| 2008/0269801 A1 | 10/2008 | Coleman et al. | |
| 2008/0269802 A1 | 10/2008 | Coleman et al. | |
| 2008/0272173 A1 | 11/2008 | Coleman et al. | |
| 2009/0069806 A1 | 3/2009 | De La Mora Levy et al. | |
| 2010/0094315 A1 | 4/2010 | Beardsley et al. | |
| 2011/0101065 A1 | 5/2011 | Milliman | |

FOREIGN PATENT DOCUMENTS

| | | |
|---|---|---|
| WO | WO 2004/096057 | 11/2004 |
| WO | WO 2007/147439 A1 | 12/2007 |

* cited by examiner

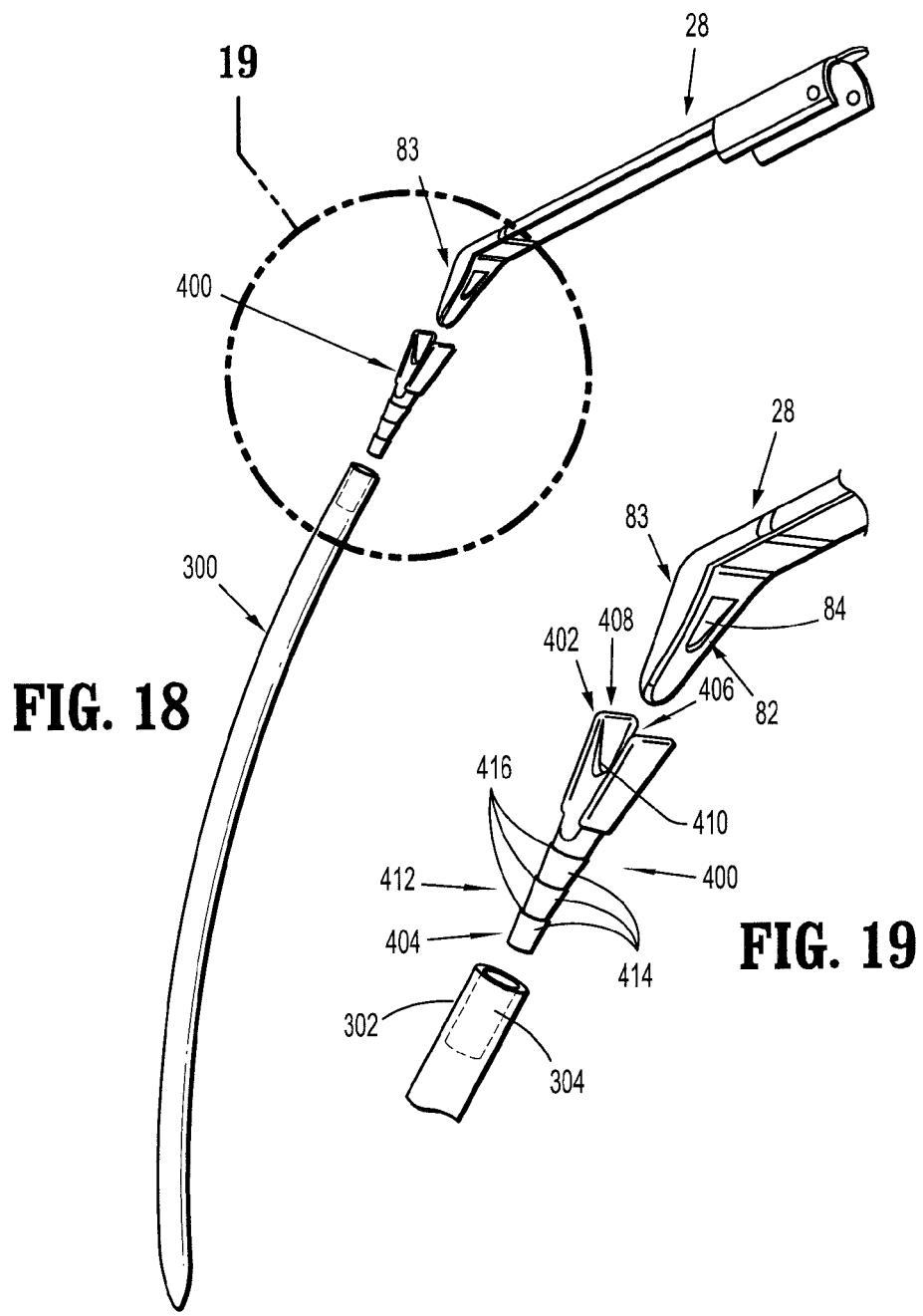

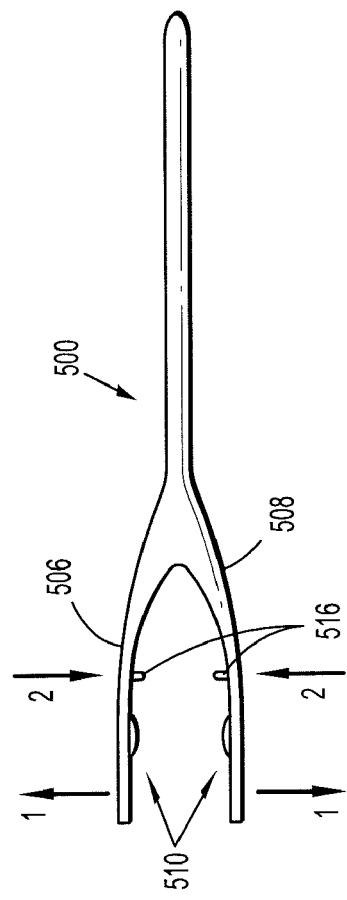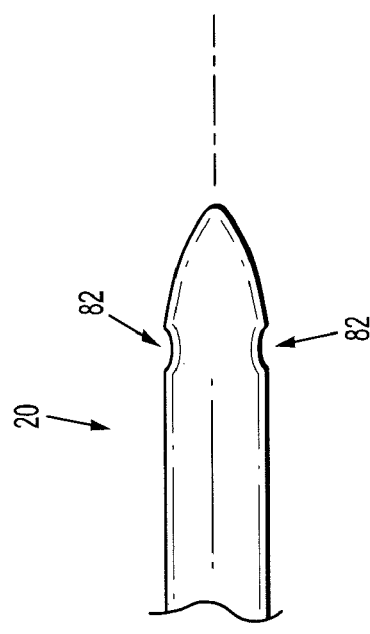
FIG. 21

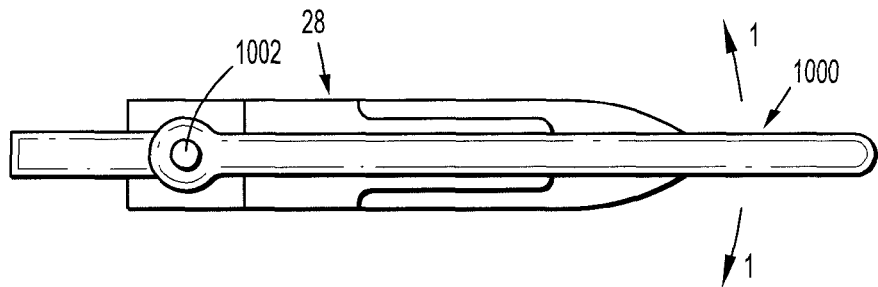
FIG. 39
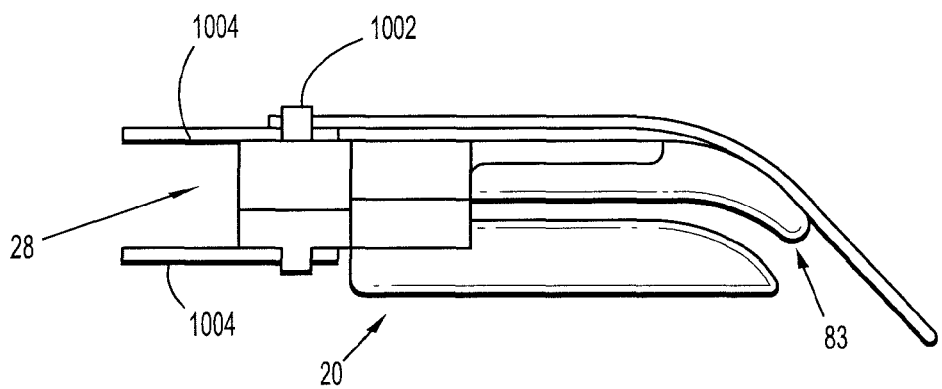
FIG. 40
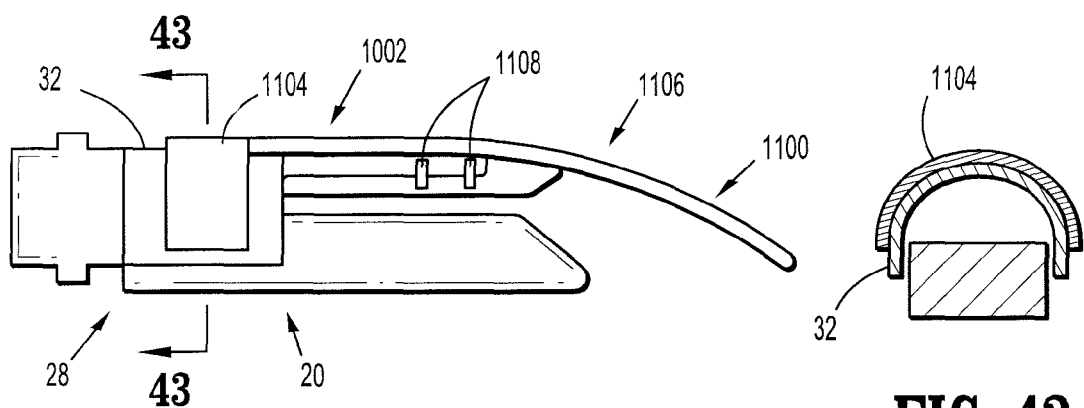
FIG. 41
FIG. 42

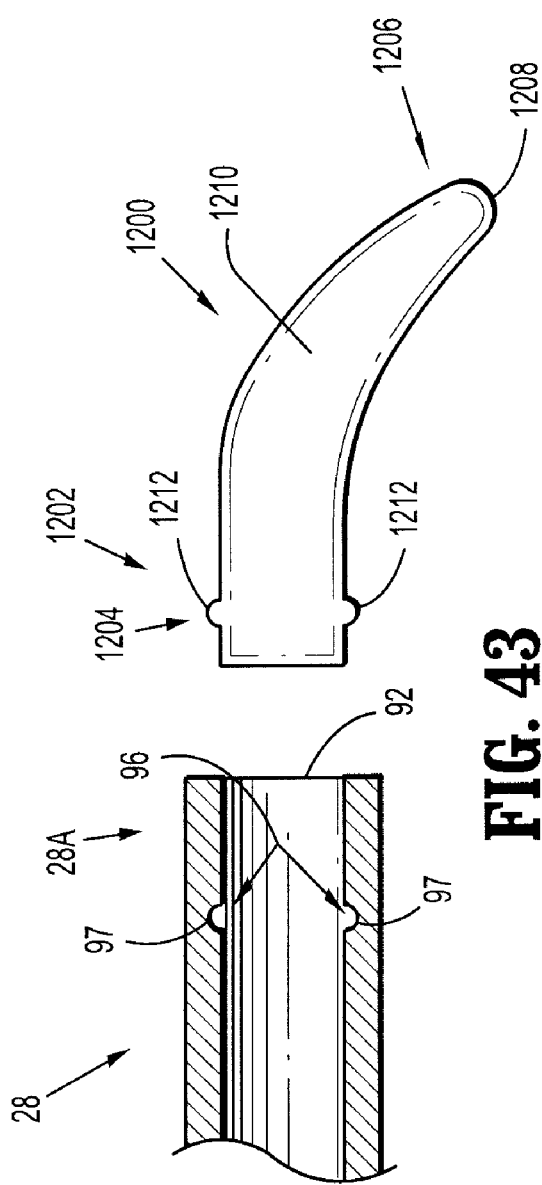
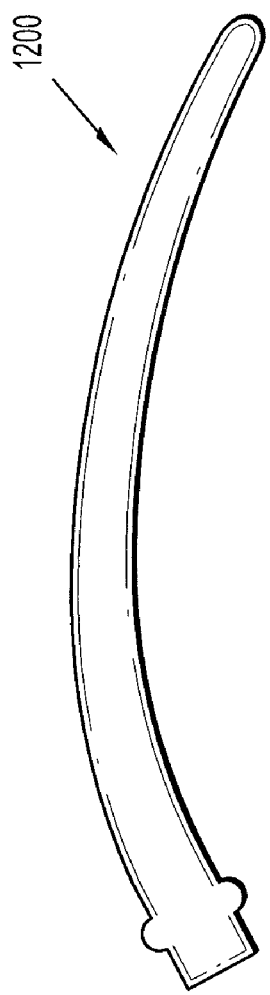
FIG. 43
FIG. 43A

DISSECTION TIP AND INTRODUCER FOR SURGICAL INSTRUMENT

CROSS-REFERENCE TO RELATED APPLICATIONS

The present application is a divisional of U.S. patent application Ser. No. 13/371,643, filed on Feb. 13, 2012, which is a divisional of U.S. patent application Ser. No. 12/571,659, filed on Oct. 1, 2009, now U.S. Pat. No. 8,136,711 which is a continuation-in-part of U.S. patent application Ser. No. 11/851,495, filed Sep. 7, 2007, now abandoned, which claims the benefit of, and priority to, U.S. Provisional Patent Application Ser. No. 60/843,254, filed Sep. 8, 2006, now abandoned, the entire contents of each of the above-identified applications being incorporated by reference herein.

BACKGROUND

1. Technical Field

The present disclosure relates generally to an apparatus for the application of surgical fasteners to tissue. The present application also relates to flexible guide for use with a surgical fastener applying apparatus to facilitate the separation of tissue and access to internal anatomical structures.

2. Background of the Related Art

In an effort to reduce trauma and recovery time, many surgical procedures are performed through small openings in the skin, such as an incision or a natural body orifice. Generally, such procedures are referred to as "endoscopic," unless performed on the patient's abdomen, in which case the procedure is referred to as "laparoscopic." Throughout the present disclosure, the term "minimally invasive" should be understood to encompass both endoscopic and laparoscopic procedures.

During the course of minimally invasive surgical procedures, a surgical fastener applying apparatus is often employed to connect adjacent sections of tissue. Many varieties of such apparatus are known in the art, some of which are specifically adapted for use in particular surgical procedures including, but not limited to, end-to-end anastomosis, circular end-to-end anastomosis, open gastrointestinal anastomosis, endoscopic gastrointestinal anastomosis, and transverse anastomosis. Examples of suitable surgical fastener applying apparatus are disclosed in U.S. Pat. Nos. 5,915,616; 6,202,914; 5,865,361; and 5,964,394. Typically, these surgical fastener applying apparatus include a first member that is movable relative to a second member such that target tissue is positionable therebetween to facilitate grasping and/or clamping of the target tissue.

Linear surgical fastener applying apparatus generally include two elongated jaw members, one of which includes a surgical fastener cartridge housing a plurality of surgical fasteners that are arranged in two or more linear rows, and the other of which includes an anvil component with a plurality of fastener forming pockets that are configured and dimensioned to receive and form the surgical fasteners upon ejection of the fasteners from the surgical fastener cartridge. Typically, the surgical fastener applying apparatus will also include a knife that is movable between the linear rows of surgical fasteners such that the tissue being joined and/or sealed is simultaneously, or nearly simultaneously, cut upon actuation of the surgical fastener applying apparatus. Given this capability, surgical fastener applying apparatus of the linear variety are commonly used during surgical procedures to simultaneously seal and cut target tissue, e.g., a patient's vasculature, organs, or the like.

It is not uncommon that certain collateral tissues, e.g., vasculature or other connective tissues, adhere to, or are otherwise joined with, the target tissue. Accordingly, a surgical fastener applying instrument including structure capable of separating the target tissue from these adherent collateral tissues would be desirable to facilitate isolation of the target tissue before continuing with the surgical procedure.

SUMMARY

In one aspect of the present disclosure, a surgical fastener applying apparatus is disclosed that includes an elongate body portion with proximal and distal ends, an end effector that is positioned at the distal end of the elongate body portion, and an introducer member.

The end effector includes a first jaw that is movably coupled to a second jaw such that target tissue is positionable therebetween. The first jaw of the end effector includes an anvil component, and the second jaw of the end effector includes a surgical fastener cartridge that is configured and dimensioned to retain a plurality of surgical fasteners therein. The first jaw terminates in a tapered, rigid tip having engagement structure.

The introducer member includes proximal and distal portions, and is configured and dimensioned for releasable connection with the end effector. The introducer member is at least partially formed from a flexible material, and is configured and dimensioned to separate the target tissue from collateral tissue to positioning of the target tissue between the first and second jaws of the end effector. The introducer has attachment structure at the proximal portion corresponding in configuration and dimensions to the engagement structure of the first jaw to facilitate releasable connection of the introducer member with the first jaw.

In one embodiment of the surgical fastener applying apparatus, it is envisioned that the proximal portion of the introducer member may be formed from a first material, whereas the distal portion of the introducer member may be formed from a second, different material with a lower durometer.

The proximal portion of the introducer member may be a separate part attached to the distal portion of the introducer. The proximal portion can be a conical member having ridges for frictionally engaging the distal portion.

In certain embodiments, the first jaw includes an anvil component and the second jaw includes a surgical fastener cartridge. The cartridge is configured and dimensioned to retain a plurality of surgical fasteners therein. The second jaw member may be pivotably mounted with respect to the first jaw member. In certain embodiments, the engagement structure is formed on the tip of the anvil component.

In order to facilitate connection of the introducer member to the end effector, it is envisioned that the proximal portion of the introducer member may include a hollow that is configured and dimensioned to at least partially receive one of the first jaw and the second jaw. To enhance the connection between the introducer member and the end effector, the engagement structure included on the end effector and the attachment structure included on the introducer member may be configured and dimensioned for connection in snap-fit arrangement. For example, the engagement structure provided on the end effector may include one or more recesses, and the attachment structure may include one or more detents that are configured and dimensioned for releasable positioning within the recess(es). When included, the recess(es) and the detent may be configured and dimensioned to provide the clinician with an audible, or tactile, indication upon successful connection of the introducer member to the end effector.

In certain embodiments, the introducer member is longer than a length of the first jaw member.

In another aspect of the present disclosure, a surgical fastener applying apparatus is disclosed that includes an elongate body portion with proximal and distal ends, an end effector that is positioned at the distal end of the elongate body portion, a connector member with proximal and distal ends that is configured and dimensioned for releasable engagement with the end effector, and an introducer member with proximal and distal portions that is configured and dimensioned for releasable engagement with the connector member. One of the first jaw and the second jaw terminates in a dissector tip and the connector member is engaged with the end effector at the dissector tip.

The end effector includes a first jaw that is movably coupled to a second jaw such that target tissue is positionable therebetween. For example, the first jaw may include an anvil component, and the second jaw may include a surgical fastener cartridge that is configured and dimensioned to retain a plurality of surgical fasteners.

The proximal end of the connector member may include first attachment structure, and the distal end of the connector member may include second attachment structure. To facilitate attachment of the connector member to the end effector, it is envisioned that at least one of the first and second jaws of the end effector may include first engagement structure, e.g., on the anvil component, that corresponds in configuration and dimensions to the first attachment structure included at the proximal end of the connector member. For example, the dissector tip includes the first engagement structure. Similarly, to facilitate attachment of the connector member to the introducer member, it is envisioned that the proximal end of the introducer member may include second engagement structure for engaging the second attachment structure. For example, it is contemplated that the first attachment structure and the first engagement structure may be configured and dimensioned for connection in snap-fit arrangement. Additionally, or alternatively, the first attachment structure and the first engagement structure may be configured and dimensioned to provide the clinician with an audible, or tactile, indication upon successful connection of the connector member and the end effector.

In certain embodiments, the first jaw includes an anvil component and the second jaw includes a surgical fastener cartridge that retains a plurality of surgical fasteners. The dissector tip may form the terminal end of the first jaw. The first engagement structure may be formed on the anvil component.

The introducer member is configured and dimensioned to separate target tissue from collateral tissue prior to positioning of the target tissue between the first and second jaws of the end effector. To facilitate connection of the introducer member and the connector member, it is envisioned that the proximal portion of the introducer member may include a hollow that is configured and dimensioned to at least partially receive the second attachment structure of the connector member. It is further envisioned that the proximal end of the introducer member may be at least partially formed from a flexible material such that receipt of the second attachment structure of the connector member causes outward expansion of the proximal end of the introducer member to create an interference fit between the introducer member and the connector member. In certain embodiments, the connector member defines ridges for frictionally engaging the proximal portion of the introducer member.

In yet another aspect of the present disclosure, a flexible guide is disclosed for use with a surgical fastener applying apparatus that includes an end effector with first and second movable jaws, and the flexible guide is configured and dimensioned to separate target tissue from collateral tissue prior to positioning of the target tissue between the first and second jaws. The flexible guide is longer than each of the first and second jaws, and has a connector member configured and dimensioned for releasable, contemporaneous engagement with a dissector tip of the end effector and with an introducer member such that the connector member is positionable between the end effector and the introducer member. The connector member is formed from a biocompatible material that is relatively more rigid than the introducer member.

In one embodiment, it is envisioned that the connector member may include a proximal end with first attachment structure and a distal end with second attachment structure. In this embodiment, the first attachment structure corresponds in configuration and dimensions to first engagement structure associated with at least one of the first and second jaws of the end effector, and the second attachment structure corresponds in configuration and dimensions to second engagement structure associated with the introducer member. The introducer member may be at least partially formed from a flexible material.

These and other features of the presently disclosed surgical fastener applying apparatus, introducer member, and connector member will become more readily apparent to those skilled in the art through reference to the detailed description of various embodiments of the present disclosure that follows.

BRIEF DESCRIPTION OF THE DRAWINGS

Various embodiments of the present disclosure are described herein below with references to the drawings, wherein:

FIG. 18 is a partial, bottom, perspective view illustrating the end effector of the surgical fastener applying apparatus, one embodiment of the presently disclosed introducer member, and a connector member that is positionable between the end effector and the introducer member;

FIG. 19 is an enlarged view of the area of detail indicated in FIG. 18;

FIG. 21 is a partial, top, plan view illustrating an alternative embodiment of the introducer member shown in FIG. 20;

FIG. 39 is a partial, top view of the anvil component including an alternative embodiment of the presently disclosed introducer member;

FIG. 40 is a partial, side view of the anvil component and the introducer member shown in FIG. 39;

FIG. 41 is a partial, side view of the anvil component including yet another embodiment of the presently disclosed introducer member;

FIG. 42 is a cross-sectional view of the anvil component and the introducer member taken along line 42-42 in FIG. 41;

FIG. 43 is a partial, top, schematic view of the anvil component and the introducer member according to another embodiment of the present disclosure;

FIG. 43A is a side view of another embodiment of the presently disclosed introducer member for use with the anvil component seen in FIG. 43;

DETAILED DESCRIPTION OF PREFERRED EMBODIMENTS

Figure 1:
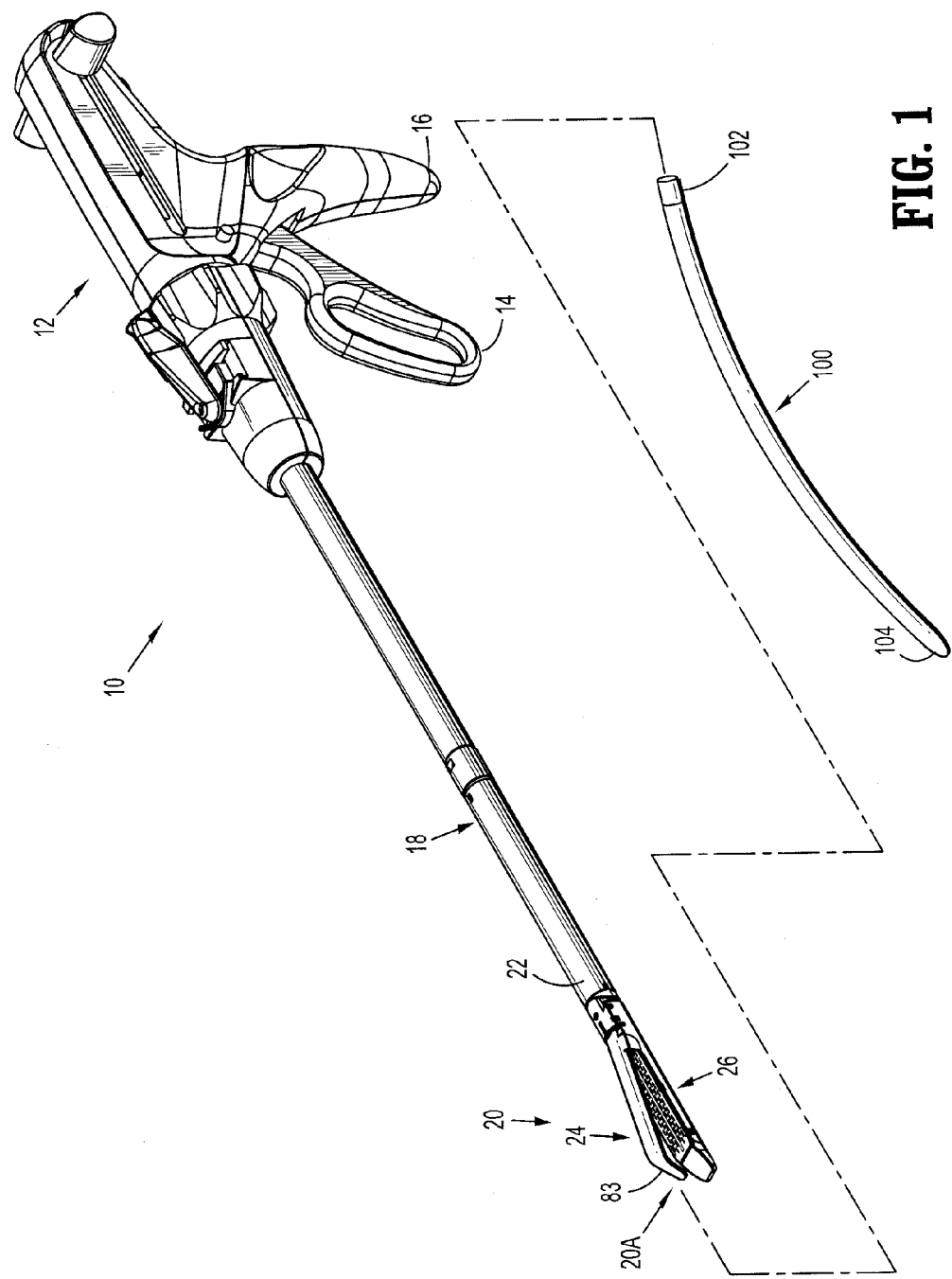
FIG. 1 is a side, perspective view of a surgical fastener applying apparatus including an end effector at a distal end thereof that is configured and dimensioned for releasable connection to an introducer member in accordance with one embodiment of the present disclosure.

Various embodiments of the presently disclosed surgical fastener applying apparatus, introducer member, connector member, and methods of using the same will now be described in detail with reference to the drawings wherein like references numerals identify similar or identical elements. In the drawings, and in the following description, the term "proximal" should be understood as referring to the end the surgical fastener applying apparatus, introducer member, or connector member discussed below, or component thereof, that is closer to the clinician during proper use, while the term "distal" should be understood as referring to the end that is further from the clinician, as is traditional and conventional in the art. In addition, the term "surgical fastener" should be understood to include any substantially rigid structure formed of a biocompatible material that is suitable for the intended purpose of joining tissue together, including but not being limited to surgical staples, clips, and the like. Moreover, the term "tissue" should be understood as referring to any human or animal tissue, artery, vein, organ, or other such anatomical structure found within the body. Specifically, use of the term "target tissue" herein below identifies the tissue that is the target, or subject, of the surgical procedure, whereas use of the term "collateral tissue" refers to any tissue surrounding the target tissue that is not the subject of the surgical procedure.

FIG. 1 illustrates a surgical fastener applying apparatus 10, of either the re-usable or disposable variety, that includes a handle assembly 12 with a movable handle 14 and a stationary handle 16, an elongated shaft 18 that extends distally from the handle assembly 12, an end effector 20 that is positioned at a distal end 22 of the elongated shaft 18, and an introducer member 100 that is releasably connectable to the end effector 20.

In various embodiments, it is envisioned that the handle assembly 12 may include motor-driven, hydraulic, ratcheting, or other such mechanisms to facilitate actuation of the surgical fastener applying apparatus 10.

In general, the end effector 20 is adapted to clamp, fasten together, and sever adjacent tissue segments along a cut-line. During use, the surgical fastener applying apparatus 10 is approximated and fired similarly to, and in accordance with, other known surgical fastener applying apparatus. A discussion of the approximation and firing of surgical fastener applying apparatus 10, including the components and interaction of the handle assembly 12 and included drive assembly, is provided below. However, additional details regarding approximation and firing of surgical fastener applying apparatus 10 may also be obtained through reference to commonly assigned U.S. Pat. No. 5,865,361, currently assigned to Tyco Healthcare Group LP, the entire contents of which are hereby incorporated by reference in their entirety.

Figure 2:
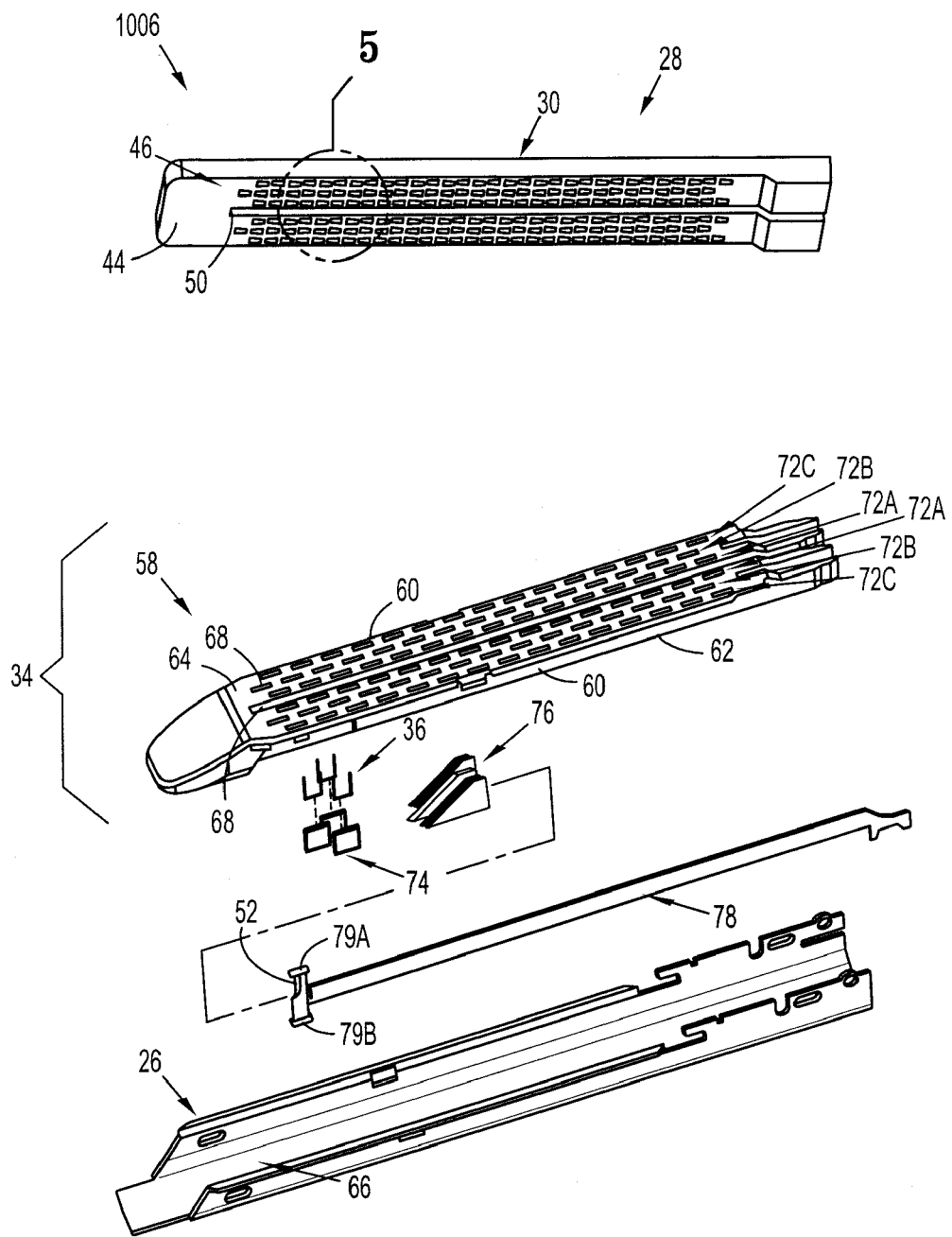
FIG. 2 is a partial, perspective view of the end effector seen in FIG. 1 with parts separated illustrating an anvil component and a surgical fastener cartridge.
Figure 3:
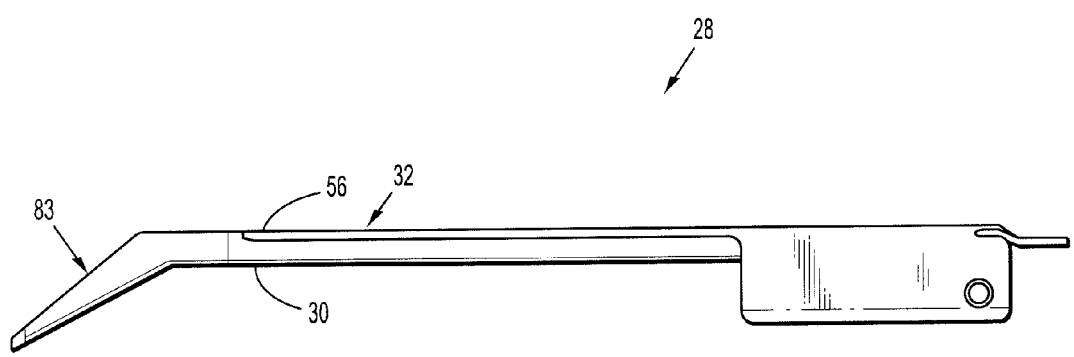
FIG. 3 is a side, plan view of the anvil component illustrating an anvil plate and an anvil cover.
Figure 4:
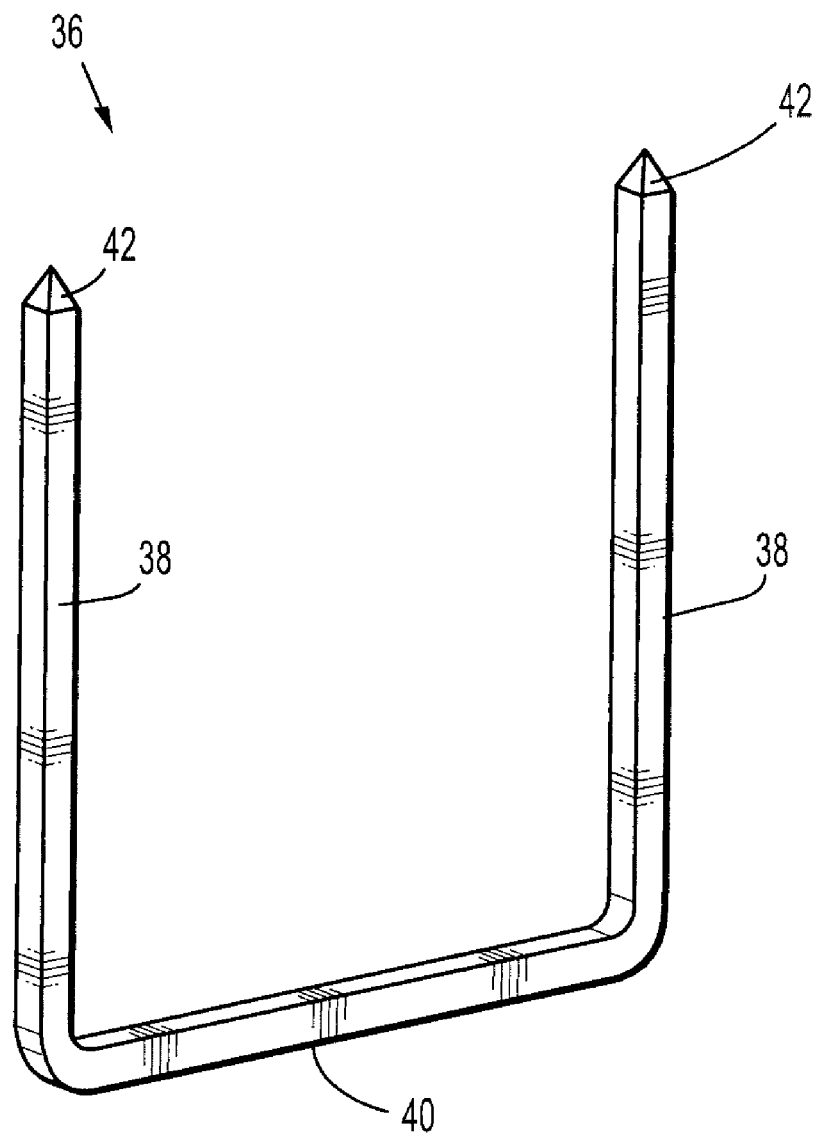
FIG. 4 is a side, perspective view of a surgical fastener for use with the presently disclosed surgical fastener applying apparatus.

Referring now to FIGS. 2-6 as well, the end effector 20 includes a first jaw 24 that is pivotally coupled to a second jaw 26 to facilitate approximation thereof, and is adapted to clamp, fasten together, and sever adjacent tissue segments along a cut-line. The first jaw 24 of the end effector 20 includes an anvil component 28 comprising an anvil plate 30 (FIGS. 2, 3) and an anvil cover 32 (FIG. 3), and the second jaw 26 includes a surgical fastener cartridge 34 (FIG. 2) that is loaded with a plurality of surgical fasteners 36 (FIGS. 2, 4). Pivoting the movable handle 14 (FIG. 1) towards the stationary handle 16 approximates the first jaw 24 and the second jaw 26. After the jaws 24, 26 are approximated, i.e., brought into close operative alignment, continued pivoting of the movable handle 14 ejects the plurality of surgical fasteners 36 (FIGS. 2, 4) from the surgical fastener cartridge 34 (FIG. 2) such that the plurality of surgical fasteners 36 are driven into the anvil plate 30, thus being formed into completed surgical fasteners, as described below. Further details regarding ejection of the surgical fasteners 36 are also provided below.

It is envisioned that the surgical fastener cartridge 34 may be removable and replaceable with another loaded cartridge. In other embodiments, the present disclosure contemplates that the end effector 20 may constitute a component of a removable and replaceable loading unit for the surgical fastener applying apparatus 10.

With reference now to FIG. 4, each surgical fastener 36 loaded into the surgical fastener cartridge 34 (FIG. 2) includes two legs 38 that are connected by a backspan 40 extending therebetween. The legs 38 extend from the backspan 40 to penetrating ends 42 that are configured and dimensioned to facilitate passage of the legs 38 through tissue. The dimensions of the backspan 40 and the legs 38 can be varied such that the surgical fastener 36 may be used to fasten tissue with varying attributes, such as tissues of different thickness, or tissues including scar tissue.

The legs 38 and the backspan 40 may define a cross-section having any suitable geometric configuration including, but not limited to, rectangular, oval, square, triangular, trapezoidal, etc. The legs 38 and the backspan 40 may exhibit the same geometrical configuration, as shown in FIG. 4, or alternatively, the legs 38 and the backspan 40 may exhibit different geometrical configurations. For example, the legs 38 may exhibit a rectangular cross-section, whereas the backspan 40 may exhibit an oval cross-section.

The penetrating ends 42 of the legs 38 may be tapered to facilitate the penetration of tissue, or alternatively, the penetrating ends 42 may not include a taper. In various embodiments, it is envisioned that the penetrating ends 42 may define either a conical surface, or flat surface.

Prior to formation, the legs 38 of each surgical fastener 36 may extend from the backspan 40 such that they are substantially parallel. In the alternative, however, the legs 38 may converge or diverge from the backspan 40.

Figure 5:
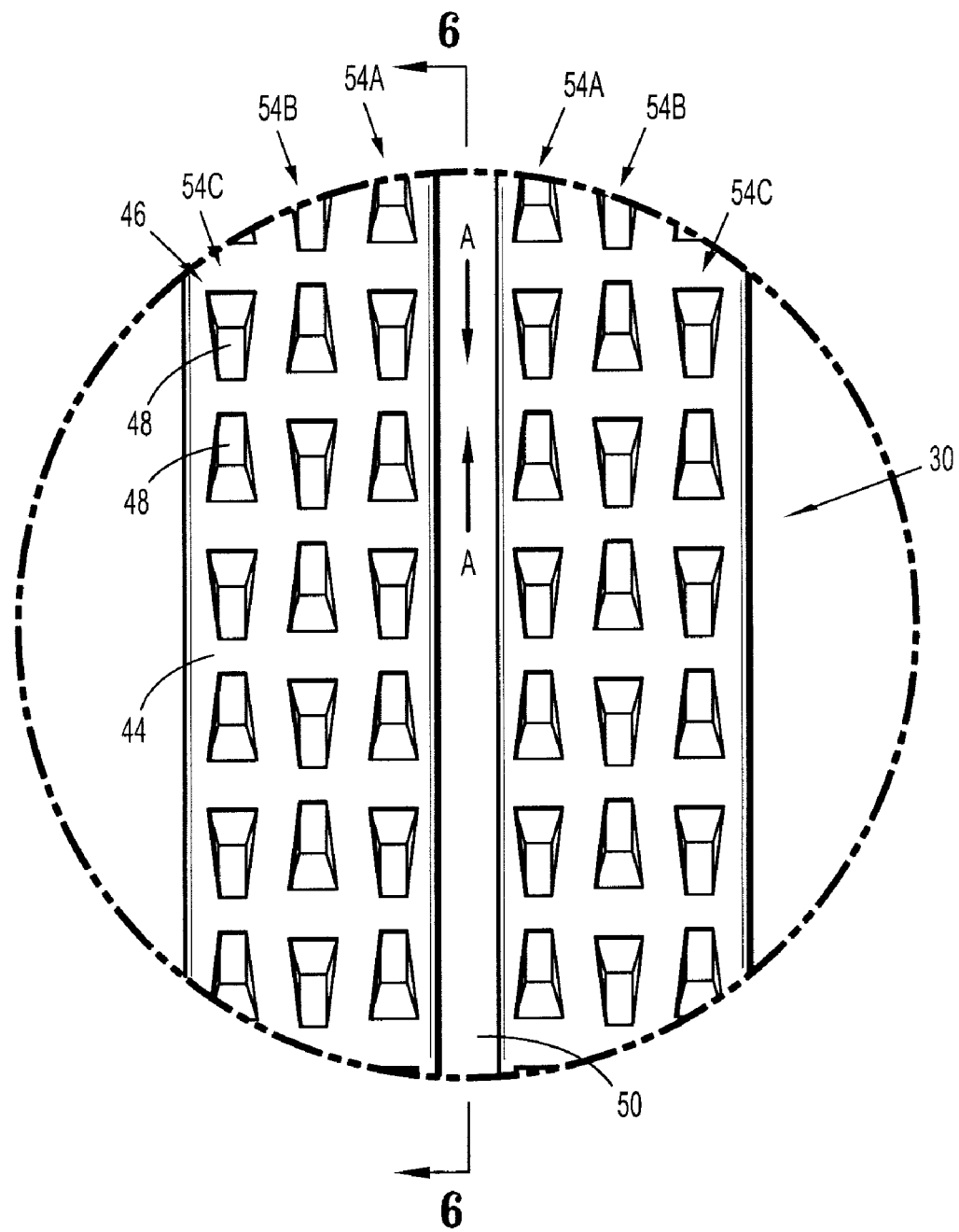
FIG. 5 is a schematic, enlarged view of the area of detail indicated in FIG. 2 illustrating a tissue contacting surface of the anvil plate and a plurality of pockets formed therein.
Figure 6:
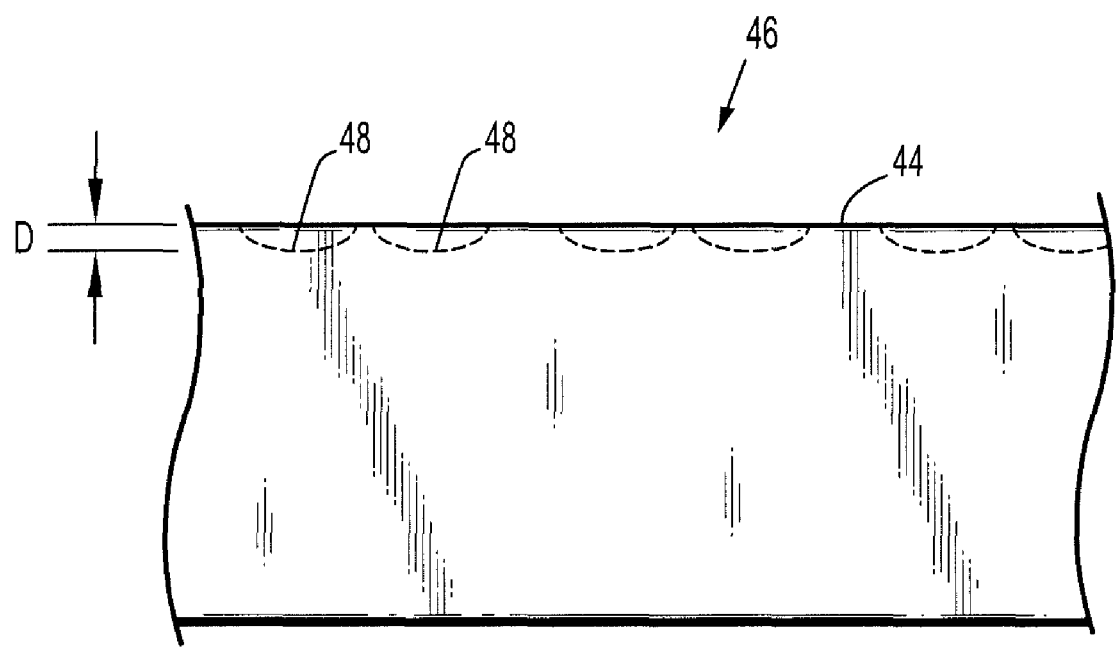
FIG. 6 is a partial, longitudinal, cross-sectional view taken along line 6-6 in FIG. 5.
Figure 7:
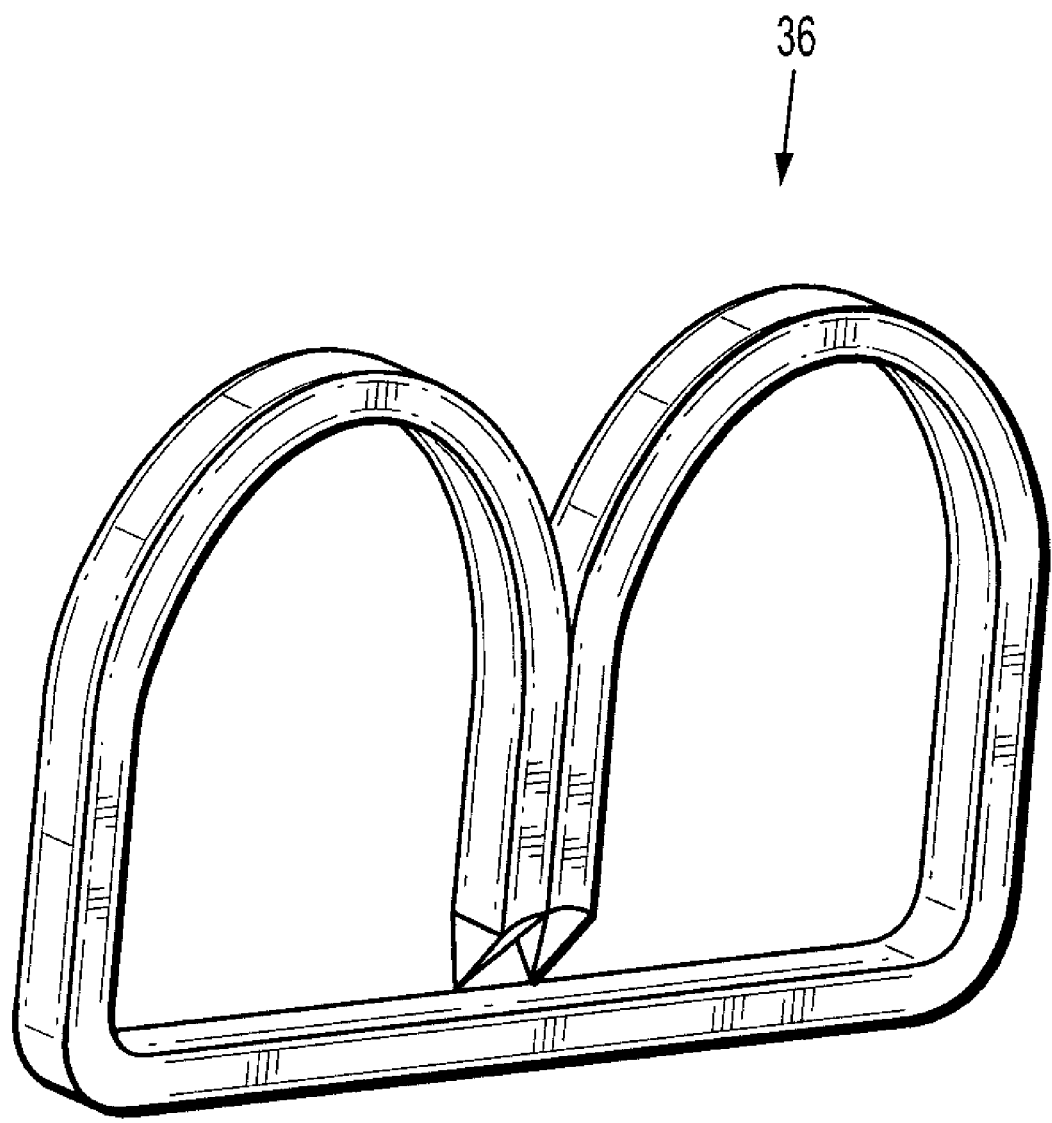
FIG. 7 is a side, perspective view of the surgical fastener shown in FIG. 4 exhibiting a standard "B" shaped configuration subsequent to formation through engagement with the pockets formed in the tissue contacting surface of the anvil plate seen in FIGS. 5 and 6.

With reference now to FIGS. 1-3 and 6 in particular, the anvil component 28 (FIG. 3) will be discussed. As mentioned above, the anvil component 28 includes the anvil plate 30 and the anvil cover 32. The anvil plate 30 is an elongated member with a tissue contacting surface 44 (FIG. 5) that includes a plurality of pockets 46 formed therein. Each of the pockets 46 is positioned to receive and deform the legs 38 (FIG. 4) of a surgical fastener 36 to achieve a formed configuration. More particularly, each pocket 46 formed in the anvil component 28 includes two forming surfaces 48 (FIG. 5) that extend into the anvil component 28, i.e., away from the tissue contacting surface 44, to define a depth "D," as best seen in FIG. 6. Upon engagement of the legs 38 with the forming surfaces 48, the forming surfaces 48 guide the legs 38 inwardly in the direction of arrows "A" (FIG. 5) to facilitate deformation of the surgical fastener 36 into a standard "B" shaped configuration (FIG. 7). In an alternative embodiment, it is envisioned that the pockets 46 formed in the tissue contacting surface 44 of the anvil plate 30 may be configured and dimensioned to deform the surgical fastener 36 so as to achieve a single-loop configuration or other shape upon formation. It should be appreciated that additional configurations and dimensions for the pockets 46 are also contemplated herein such that the surgical fasteners 36 may exhibit other configurations upon formation.

The pockets 46 are arranged into rows disposed on opposite sides of a slot 50 (FIGS. 2, 5) extending through the anvil plate 30. The slot 50 is configured to accommodate movement of a knife 52 (FIG. 2), or other such cutting element, in order to facilitate severing of tissue along a cut-line. Although the slot 50 is depicted as extending longitudinally through the anvil plate 30, in alternative embodiments, it is envisioned that the slot 50 may define a configuration that is angled, arcuate, or shaped otherwise. The slot 50 may extend along a centerline of the anvil plate 30, as shown in the embodiment illustrated in FIGS. 2 and 5, or alternatively, the slot 50 may be offset from the centerline of the anvil plate 30.

In the embodiment of the anvil plate 30 seen in FIGS. 2 and 5, the pockets 46 formed in the tissue contacting surface 44 are arranged into a pair of inner rows 54A, a pair of intermediate rows 54B, and a pair of outer rows 54C (FIG. 4). The pair of inner rows 54A are spaced laterally outward of the slot 50 and are closest thereto, the pair of intermediate rows 54B are spaced laterally outward from the pair of inner rows 54A, and the pair of outer rows 54C are spaced laterally outward from the pair of intermediate rows 54B and are furthest from the slot 50. While the anvil plate 30 is depicted as including three pairs of rows, i.e., the respective pairs of inner, intermediate, and outer rows 54A, 54B, 54C, alternative embodiments of the anvil plate 30 including fewer and greater numbers of rows of pockets 46 are not beyond the scope of the present disclosure.

Referring now to FIG. 3, the anvil cover 32 includes an outer surface 56 and is fixed relative to the anvil plate 30 such that there is no relative movement therebetween. For example, it is envisioned that the anvil cover 32 may be secured to the anvil plate 30 in a snap-fit arrangement, via one or more welds, or in any other manner suitable for the intended purpose of establishing a secured connection therewith.

Second jaw 26 includes a surgical fastener cartridge 34 and a channel 66. The surgical fastener cartridge 34 will now be described with reference to FIG. 2. The surgical fastener cartridge 34 includes a cartridge body 58 with a pair of sidewalls 60, a bottom wall 62, and a top wall 64, and resides in the channel 66 of the second jaw 26. In the illustrated embodiment, the cartridge body 58 includes a slot 68 extending therethrough that is configured to accommodate longitudinal movement of the knife 52. As discussed above with respect to the anvil component 28, while the slot 68 is depicted as extending longitudinally through the surgical fastener cartridge 34, in alternative embodiments, the slot 68 may define a configuration that is angled, arcuate, or shaped otherwise. The position of the slot 68 corresponds to that of the slot 50 extending through the anvil plate 30 such that the slot 68 aligns with the slot 50. The slot 68 may extend along a centerline of the surgical fastener cartridge 34, as seen in FIG. 3, or alternatively, the slot 68 may be spaced therefrom.

The top wall 64 of the cartridge body 58 includes a substantially planar configuration that extends in substantially parallel relation to the tissue contacting surface 44 (FIG. 5) of the anvil plate 30, as well as a plurality of retention slots 68. The retention slots 68 are arranged into rows corresponding in position to the rows of pockets 46 (FIG. 5) formed in the tissue contacting surface 44 of the anvil plate 30. Accordingly, in the particular embodiment of the surgical fastener cartridge 34 seen in FIG. 2, the retention slots 68 are arranged into a pair of inner rows 72A, a pair of intermediate rows 72B, and a pair of outer rows 72C, each of which is disposed on opposite sides of the slot 68. The pair of inner rows 72A are spaced laterally outward of the slot 68 and are closest thereto, the pair of intermediate rows 72B are spaced laterally outward from the pair of inner rows 72A, and the pair of outer rows 72C are spaced laterally outward from the pair of intermediate rows 72B and are furthest from the slot 68. While the surgical fastener cartridge 34 is depicted as including three pairs of rows, i.e., the respective inner, intermediate, and outer rows 72A, 72B, 72C, alternative embodiments of the surgical fastener cartridge 34 including fewer and greater numbers of rows of fastener retention slots 68 are not beyond the scope of the present disclosure.

Each fastener retention slot 68 is configured and dimensioned to receive a surgical fastener 36 (FIGS. 2, 4), as well as a correspondingly dimensioned pusher 74 (FIG. 2) positioned therein. During use, the pushers 74 are driven upwardly, i.e. towards the top wall 64 of the cartridge body 58, by a sled 76 (FIG. 3) into engagement with the surgical fasteners 36 to thereby eject the surgical fasteners 36 from the retention slots 68, as discussed in further detail below. As the surgical fasteners 36 exit the fastener retention slots 68, they are deployed in rows, e.g., inner, intermediate, and outer rows in the illustrated embodiment, on opposite sides of the cut-line created in the tissue.

With reference now to FIGS. 1 and 8-10, one embodiment of the presently disclosed introducer member, which is identified by the reference character 100, will be discussed. The introducer member 100 includes respective proximal and distal ends 102, 104, and is formed from a pliable, biocompatible material, including but not limited to polymeric materials, such as rubbers or plastics. In one particular embodiment, it is envisioned that the introducer member 100 may be entirely formed from a flexible material. Alternatively, however, it is envisioned that the introducer member 100 may include portions of increased rigidity formed from a higher durometer material to provide additional structure to the introducer member 100, and/or assist in the separation of tissue.

Figure 8:
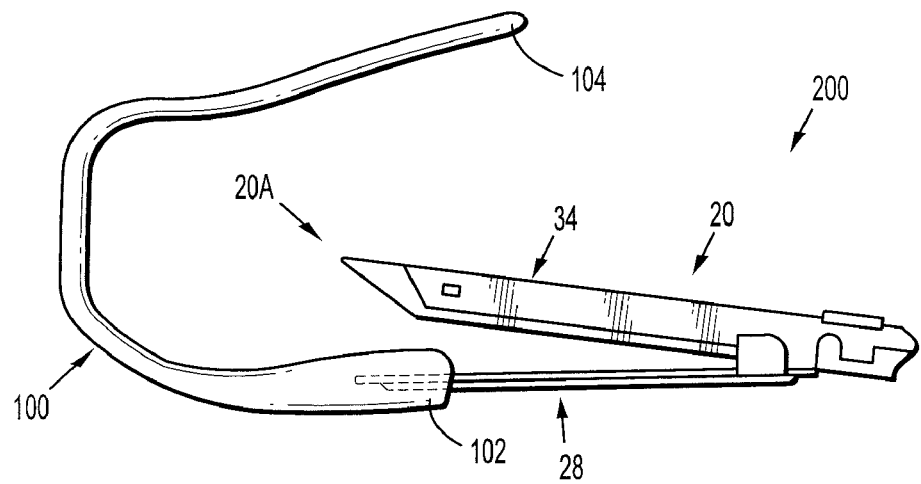
FIG. 8 is a side, plan view illustrating an introducer member attached to an end effector.
Figure 9:
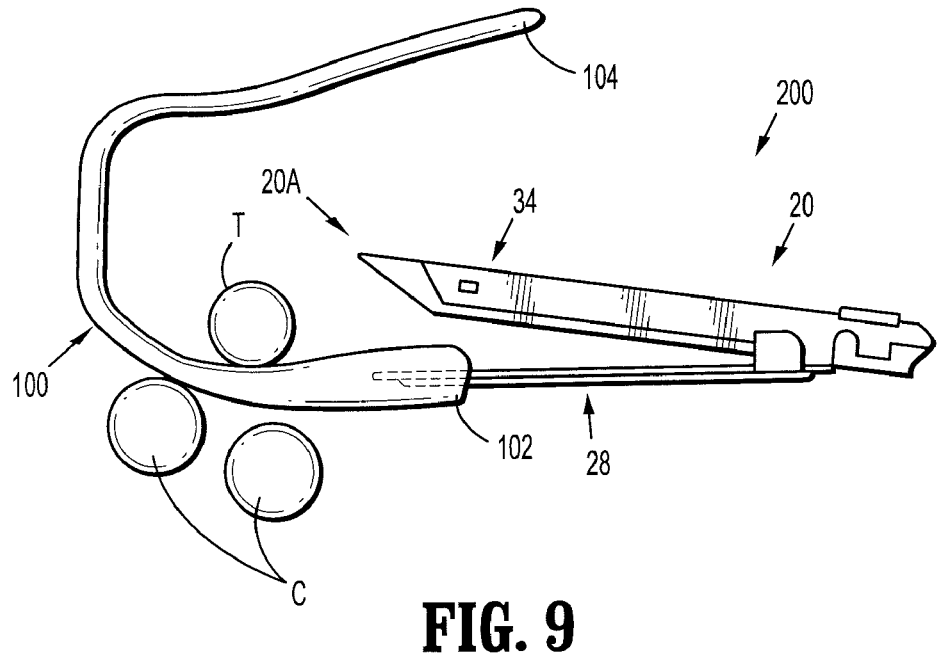
FIG. 9 is a side, plan view of the introducer member seen in FIG. 8 shown attached to the end effector, and positioned between target tissue and collateral tissue.
Figure 10:
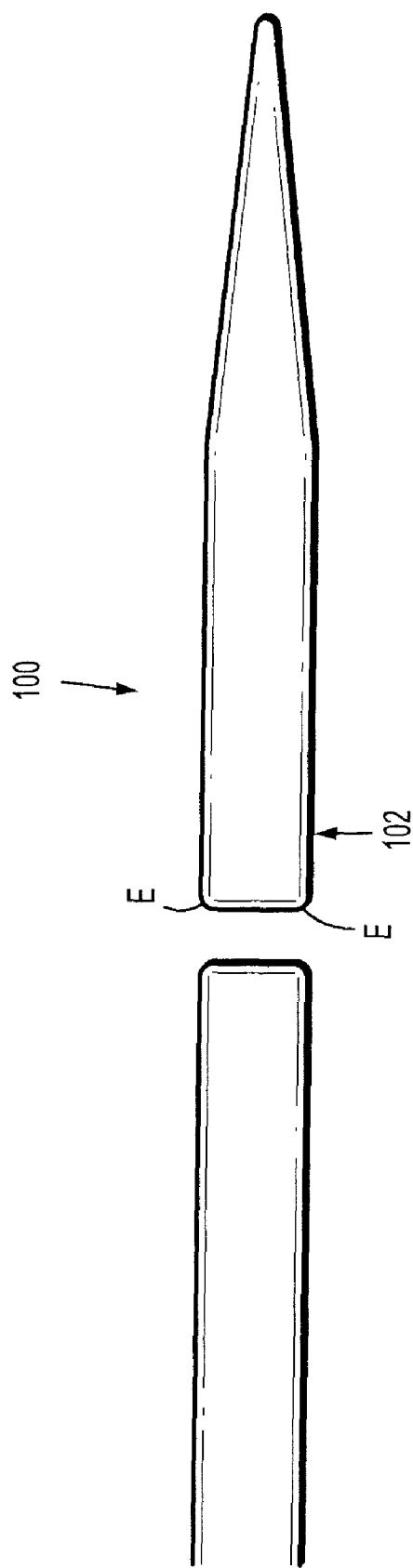
FIG. 10 is a top view illustrating one embodiment of the presently disclosed introducer member prior to attachment to the end effector.
Figure 11:
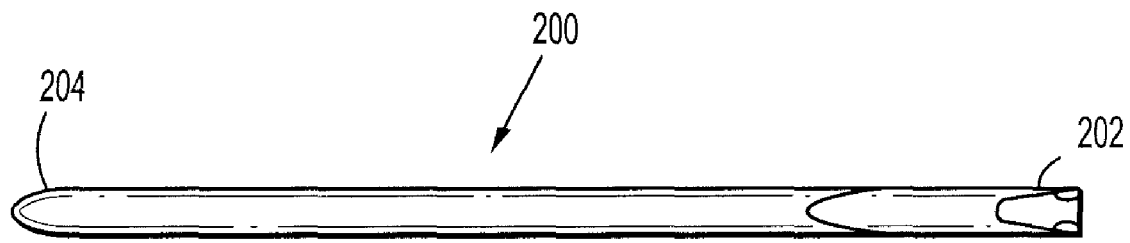
FIG. 11 is a longitudinal, cross-sectional view of an embodiment of a presently disclosed introducer member.

The open proximal end 102 of the introducer member 100 is configured and dimensioned to facilitate placement over a distal end 20A of the end effector 20. For example, as illustrated in FIGS. 8 and 9, the proximal end 102 of the introducer member 100 may be configured and dimensioned for placement about the anvil component 28, or alternatively, the proximal end 102 may be configured and dimensioned for placement about the surgical fastener cartridge 34. To facilitate connection and disconnection of the introducer member 100 to the end effector 20, it is envisioned that the proximal end 102 of the introducer 100 may include radiused edges "E," as shown in FIG. 10.

In one embodiment, it is envisioned that the introducer member 100 may be operatively connected to the handle assembly 12 (FIG. 1) of the surgical fastener applying apparatus 10 such that the introducer member 100 is steerable by the clinician. For example, the introducer member 100 may be operatively connected to the handle assembly 12 via one or more flexible members (not shown), such as cables, guidewires, or the like, that are attached at various points along the length of the introducer member 100 such that manipulation of the flexible member(s) will cause corresponding movement of the introducer member 100. For example, the flexible member(s) may be attached to the introducer member 100 such that proximal retraction of the flexible member(s) causes bending or flexing of the introducer member 100 at a predetermined location, thereby allowing the clinician to selectively reconfigure the introducer member 100, and effectively steer the introducer member 100 between the target tissue "T" (FIG. 10) and the collateral tissue "C."

The introducer member 100 is configured, dimensioned, and adapted to guide the end effector 20 into position between the target tissue "T" (FIG. 10) that is the subject of the surgical procedure, and any collateral tissue "C" surrounding the target tissue "T." To this end, the introducer member 100 may include a partially or wholly curved configuration that defines an arc substantially in the range of approximately 5° to approximately 90°. In one embodiment, for example, as shown in FIGS. 8 and 9, the introducer member 100 curves from the anvil component 28 towards the surgical fastener cartridge 34, and is longer than the jaws, so that the target tissue is approached at an angle and directed between the jaws of the surgical fastener applying apparatus. It should be appreciated, however, that the introducer member 100 may curve in any direction suitable for the intended purpose of guiding the instrument into position and/or facilitating separation of the target tissue "T" from any collateral tissue "C."

Additionally, the introducer member 100 includes an elongate profile that tapers towards the distal end 104, as seen in FIGS. 1 and 9-11. Including a tapered profile allows the distal end 104 of the introducer member 100 to define a reduced cross-sectional area when compared to more proximal portions thereof in order to facilitate advancement of the introducer member 100 through the patient's tissue. Additionally, the reduced cross-sectional area at the distal end 104 of the introducer member 100 facilitates access to internal spaces and tissues that would otherwise be inaccessible given the larger dimensions of the end effector 20 (FIG. 1), and reduces the effect that distal advancement of the surgical fastener applying apparatus 10 has upon the patient's internal tissues. For example, in one embodiment, it is envisioned that the distal end 104 of the introducer member 100 may have a transverse dimension in the range of approximately 2 mm to approximately 6 mm, although dimensions that are both larger and smaller are not beyond the scope of the present disclosure.

The introducer member 100 may have any cross-sectional configuration suitable for the intended purpose of atraumatically separating the target tissue "T" (FIG. 10) from any collateral tissue "C" in order to facilitate access to a patient's internal tissues and organs with the surgical fastener applying apparatus 10 (FIG. 1). For example, the introducer member 100 may have an oval cross-sectional configuration (see FIG. 13), a substantially rounded cross-sectional configuration, or a polygonal cross-sectional configuration.

Referring now to FIGS. 1-10, use and operation of the surgical fastener applying apparatus 10 (FIG. 1) will be discussed in connection with the introducer member 100. As mentioned above and seen in FIG. 1, the handle assembly 12 includes a movable handle 14. The movable handle 14 is operatively connected to an actuation shaft (not shown), which receives the proximal end of a control rod such that linear advancement of the actuation shaft causes corresponding linear advancement of the control rod. The control rod is further engagable with an axial drive assembly including an elongated drive beam 78 (FIG. 2) having a distal end that is configured and dimensioned to support the knife 52. The sled 76, as discussed above, drives the pushers 74 upwardly, driving the fasteners 36 against the pockets 46 of the anvil component 28. The knife 52 is positioned on the drive beam 78 to translate behind the sled 76. The drive beam 78 includes an upper flange 79A that is configured and dimensioned to move along a top surface of the anvil plate 30, and a lower flange 79B that is configured and dimensioned for movement along the outer side of the channel 66 while the drive beam moves through the slot 50 of the anvil component and the slot 68 of the channel 66.

Initially, the introducer member 100 is connected to the end effector 20 (FIG. 1, 8, 9), i.e., the introducer member 100 is positioned about the anvil component 28 or the surgical fastener cartridge 34. Thereafter, the assembly of the surgical fastener applying apparatus 10 (FIG. 1) and the introducer member 100 can be manipulated such that the distal end 104 of the introducer member 100 is positioned between the target tissue "T" (FIG. 10) and the collateral tissue "C." During manipulation of the introducer member 100, the flexible material comprising the introducer member 100 allows the introducer member 100 to gently urge the collateral tissue "C" away from the target tissue "T," thereby establishing and/or dilating a pathway along which the end effector 20 can travel.

To facilitate positioning of the target tissue "T" (FIG. 9) between the anvil component 28 and the surgical fastener cartridge 34, the distal end 104 of the introducer member 100 can be withdrawn, or pulled proximally, e.g., via the aforementioned flexible member(s) (not shown), if included. Manipulating the introducer member 100 in this manner guides the target tissue "T" into position between the anvil component 28 and the surgical fastener cartridge 34, while simultaneously protecting the collateral tissue "C" from undesirable contact with any components of the surgical fastener applying apparatus 10.

After confirming that that the target tissue "T" has been positioned as desired between the anvil component 28 and the surgical fastener cartridge 34, and confirming that the collateral tissue "C" is not located in a position that will result in damage to the target tissue "T" or the collateral tissue "C" upon actuation of the surgical fastener applying apparatus 10 (FIG. 1), the introducer member 100 can be removed from the end effector 20. Thereafter, the jaws 24, 26 (FIG. 1) are approximated using the handle assembly 12 to clamp the target tissue "T" (FIG. 9) therebetween, and apply a compressive force thereto. Specifically, manipulation of the movable handle 14 advances the actuation shaft to effectuate corresponding advancement of the control rod. In particular embodiments, the actuation shaft includes a toothed rack defined thereon, and the movable handle 14 has a ratcheting pawl mounted thereto for incrementally engaging and advancing the actuation shaft. The pawl may be mounted on a pivot pin and a coiled torsion spring may be provided to bias the pawl into engagement with the toothed rack. The control rod is connected at its distal end to the axial drive assembly, which includes the aforementioned drive beam 78 (FIG. 2), such that distal movement of control rod effects distal movement of the drive beam 78, which in turn, forces the anvil component 28 (FIG. 2) towards the surgical fastener cartridge 34. Specifically, the control rod advances the drive beam 78 distally such that the upper flange 79A traverses the top surface of the anvil plate 30, and the lower flange 79B traverses the channel 66 extending through the surgical fastener cartridge 34.

With the tissue securely clamped between the jaws 24, 26 (FIGS. 1, 2), the surgical fastener applying apparatus 10 is fired to eject the surgical fasteners 36 (FIG. 2). The surgical fastener applying apparatus 10 is approximated and fired similarly to, and in accordance with other known surgical fastener applying apparatus, such as, for example, the surgical fastener applying apparatus disclosed in commonly assigned U.S. Pat. No. 5,865,361, which is currently assigned to Tyco Healthcare Group LP, the disclosure of which is hereby incorporated by reference herein in its entirety. Specifically, the movable handle 14 is manipulated to cause advancement of the drive assembly, which causes the sled 76 (FIG. 2) to traverse the cartridge body 58 and engage the pushers 74 to thereby eject the plurality of surgical fasteners 36 from the surgical fastener cartridge 34. During distal advancement of the sled 76, angled leading surfaces thereof sequentially contact cam surfaces included on the pushers 74. The interaction between the leading surfaces of the sled 76 and the cam surfaces of the pushers 74 urges the pushers 74 towards the top wall 64 of the cartridge body 58 to eject the surgical fasteners 36 from the retention slots 68 formed in the cartridge body 58. Sequential firing of the surgical fasteners 36 continues until the sled 76 is advanced to the distal end of the surgical fastener cartridge 34, at which time all of the surgical fasteners 36 housed within the surgical fastener cartridge 34 will have been ejected.

During ejection, the plurality of surgical fasteners 36 pass through the retention slots 68 through the target tissue "T," and into engagement with the pockets 46 (FIGS. 2, 5) defined in the tissue contacting surface 44 of the anvil component 28. Engagement of the surgical fasteners 36 with the pockets 46 forms the surgical fasteners 36 to thereby connect adjacent portions of the target tissue "T" (FIG. 9).

Referring now to FIGS. 11-48, alternative embodiments of the presently disclosed introducer member will be discussed.

Each embodiment of the introducer member discussed herein below is similar to the aforedescribed introducer member 100, and accordingly, will only be discussed with respect to any differences therefrom.

With specific reference to FIGS. 11-14, an embodiment of the introducer member identified by the reference character 200 will be discussed. The introducer member 200 may be entirely or partially hollow or solid, and includes an open proximal end 202, and a closed distal end 204. When configured as a solid member, interior surfaces of the open proximal end 202 may be shaped to abut exterior surfaces of the anvil component 28 (FIG. 3) to provide stability and support for the introducer member 200.

To facilitate distal advancement and navigation of the introducer member 200 between the target tissue "T" (FIG. 9) and the collateral tissue "C," it is envisioned that the introducer member 200 may include a dual taper. Specifically, the introducer member 200 may include a tapered profile that decreases in cross-sectional height and width from the proximal end 202 to the distal end 204.

Figure 12:
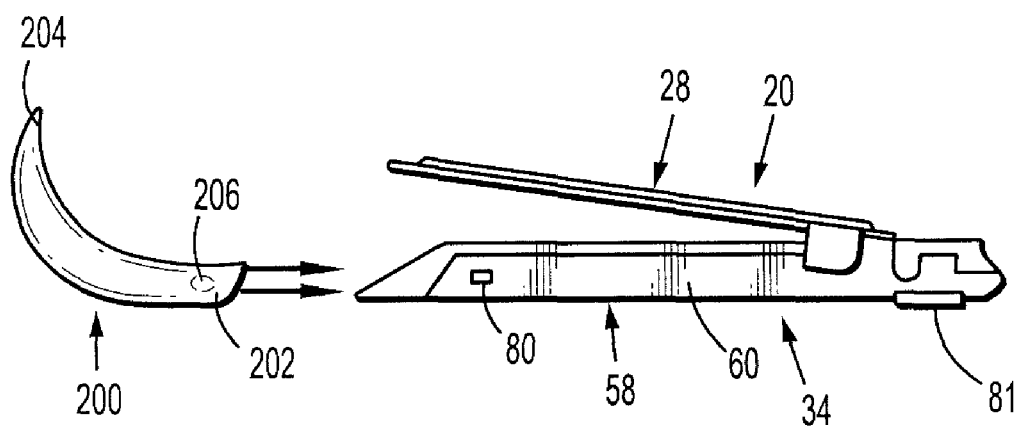
FIG. 12 is a side, plan view illustrating another introducer member before attachment to an end effector.
Figure 13:
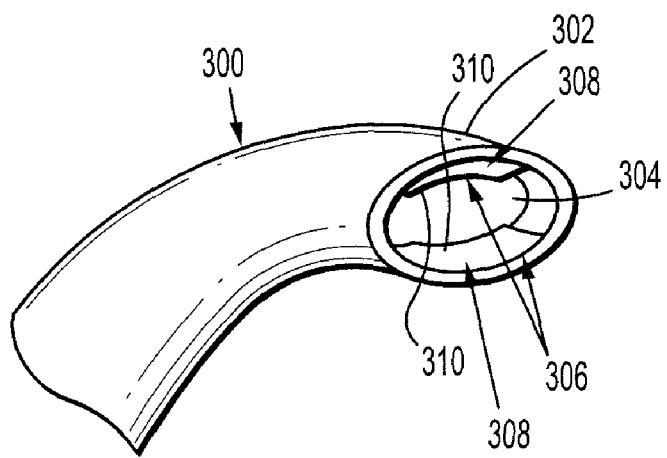
FIG. 13 is a partial, rear, perspective view illustrating a proximal end of the presently disclosed introducer member according to an embodiment of the present disclosure.

The open proximal end 202 of the introducer member 200 is configured, dimensioned, and adapted to facilitate slidable engagement and disengagement with the end effector 20 (FIGS. 1, 12). For example, the open proximal end 202 of the introducer member 200 may be configured and dimensioned to frictionally engage the surgical fastener cartridge 34, as shown in FIG. 13, or alternatively, the open proximal end 202 of the introducer member 200 may be configured and dimensioned to frictionally engage the anvil component 28 (FIG. 3), e.g., in a manner similar to that discussed above with respect to the introducer member 100 (FIGS. 1-11).

To ensure proper operation of the end effector 20 (FIGS. 1, 12) without having to remove the introducer member 200 prior to actuation of surgical fastener applying apparatus 10 (FIG. 1), it is envisioned that the portion of the introducer member 200 positioned between the anvil component 28 (FIG. 12) and the surgical fastener cartridge 34 may have a thickness less than the designed gap between the anvil component 28 and the surgical fastener cartridge 34, thus inhibiting interference with the anvil component 28 upon actuation of the surgical fastener applying apparatus 10. Additionally, or alternatively, it is envisioned that the proximal end 202 of the introducer member 200 may include a cutout (not shown) that is positionable between the anvil plate 30 and the surgical fastener cartridge 34.

To facilitate engagement with, and disengagement from, the end effector 20 (FIGS. 1, 12), it is envisioned that the introducer member 200 may incorporate an adhesive, or alternatively, that the introducer member 200 may include structure that is configured and dimensioned for engagement with corresponding structure formed on the end effector 20. For example, the introducer member 200 may include structure, e.g., projections 206 (FIG. 13), formed on opposing surfaces within the proximal end 202 that is configured and dimensioned for engagement with corresponding structure on the end effector 20, e.g., with notches 80 formed in the sidewalls 60 of the cartridge body 58. Typically, the notches 80 formed in the sidewalls 60 cartridge body 58 are configured and dimensioned for engagement with corresponding structure (not shown) on the second jaw 26 (FIG. 1) to assist in secured placement of the surgical fastener cartridge 34. In this embodiment, during use, the introducer member 200 is positioned about the distal end of the surgical fastener cartridge 34 until the projections 206 within the proximal end 202 of the introducer member 200 engage the notches 80. To remove the introducer member 200, the clinician applies a force sufficient to deform the proximal end 202 of the introducer member 200 such that the proximal end 202 flexes outwardly, thereby disengaging the projections 206 from the notches 80. Subsequently, the introducer member 200 can be removed from the surgical fastener cartridge 34.

It is envisioned that that the introducer member 200 may include one or more recessed portion(s), cutouts, or the like (not shown) to inhibit interference with movable structure of the end effector 20, such as a flange 81 (FIG. 12) formed on the surgical fastener cartridge 34. In the illustrated embodiment of the surgical fastener cartridge 34, the flange 81 is configured and dimensioned for longitudinal, slidable movement towards the distal end of the surgical fastener cartridge 34 as the anvil component 28 is progressively clamped to balance clamping forces generated within the end effector 20.

Although each embodiment of the presently disclosed introducer has been discussed hereinabove as being a removable component of the surgical fastener applying apparatus 10 (FIG. 1), it is also envisioned that either of the introducer members 100, 200 may be integrally formed with the end effector 20, such that the introducer members 100, 200 are not detachable from the end effector 20.

As discussed above with respect to the introducer member 100 (FIGS. 1-10), it is envisioned that the introducer member 200 may be operatively connected to the handle assembly 12 (FIG. 1) of the surgical fastener applying apparatus 10 via a linkage, e.g., cables, bands, or the like, to facilitate selective reconfiguration of the introducer member 200.

In addition to being steerable, it is envisioned that the introducer member 200 may be biased towards a curved configuration (FIG. 12) relative to the component of the end effector 20 (FIGS. 1, 12) to which the introducer member 200 is attached, e.g., the anvil component 28 (FIG. 12) or the surgical fastener cartridge 34, or alternatively, that the introducer member 200 may be biased towards a linear position (FIG. 12)

Figure 14:
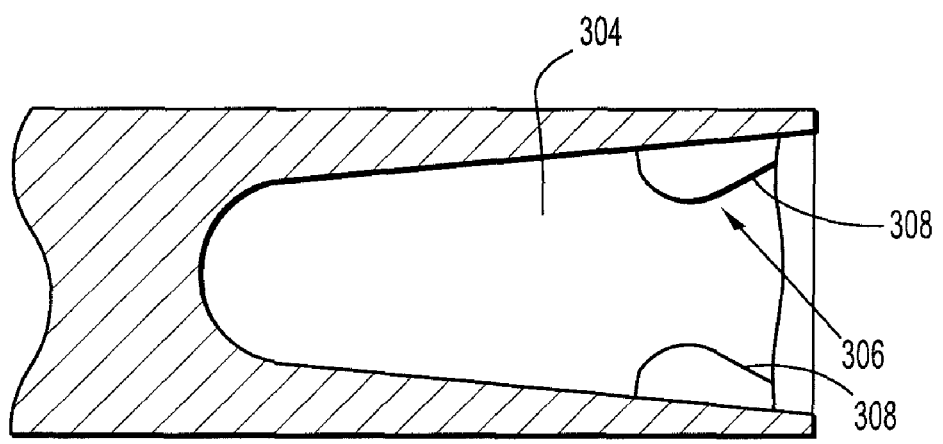
FIG. 14 is a partial, longitudinal, cross-sectional view of the proximal end of the introducer member shown in FIG. 13.
Figure 15:
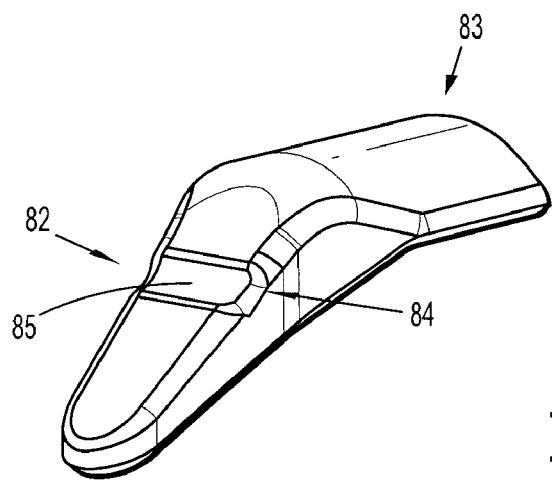
FIG. 15 is a top, perspective view of one embodiment of a dissector portion or dissector tip included on the anvil component of the end effector.

Referring now to FIGS. 13-15, an embodiment of the presently disclosed introducer, which is identified by the reference character 300, will be discussed. During certain procedures, certain vasculature or other adherent connective, joined or other tissue, adheres or is joined with the target tissue, i.e., the tissue to be stapled and severed. If such tissue must be separated before accessing the target tissue, separating the tissue and guiding the surgical fastening apparatus into place so that the target tissue is directed between the jaws, while the collateral tissue is avoided, it is advantageous to include a dissector portion or dissector tip 85 on one of the jaws. In a certain preferred embodiment, the dissector tip 85 is a rigid, tapered tip that is integral with or attached to the anvil component of the surgical fastening apparatus. Such a dissector tip 85 can be seen in FIG. 16. The dissector tip 85 is desirably curved or angled so as to approach the surgical fastener cartridge 34 so that when tissue is approached at an angle, the tissue is directed between the jaws.

The introducer 300 includes a proximal end 302 defining a hollow 304 that is configured and dimensioned to at least partially receive the dissector tip of the anvil component 28 (FIGS. 2, 3). As illustrated in FIGS. 13-15, for example, the hollow 304 is configured and dimensioned to receive a portion of the anvil component 28, and more specifically, an optional dissector portion 83 or tip 85 of the anvil component 28 (FIGS. 1, 3, 15). The introducer 300 provides a flexible, longer guide for the surgical fastener apparatus and extends the access of the apparatus, while more gradually guiding the apparatus toward the target tissue. The introducer 300 is flexible, in contrast to the rigid dissector tip, to give the user more options in how to approach the tissue. If the user prefers, the introducer 300 can be attached to the dissector tip, or removed so that the dissector tip can be used to approach, access and separate tissue while guiding the tissue into place between the jaws.

Figure 16:
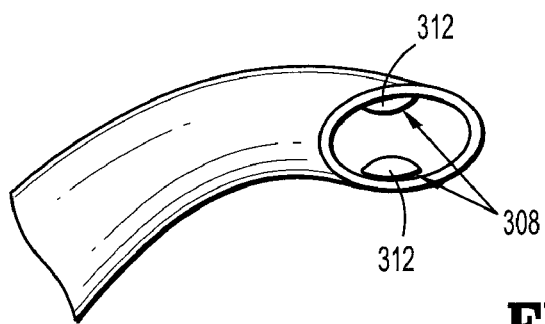
FIG. 16 is a partial, rear, perspective view illustrating a proximal end of the presently disclosed introducer member according to another embodiment of the present disclosure.

To facilitate connection between the introducer member 300 and the end effector 20 (FIG. 1), the proximal end 302 of the introducer member 300 includes attachment structure 306 (FIG. 13) that is configured and dimensioned for releasable connection with corresponding engagement structure 82 (FIG. 15) included on the dissector portion of the end effector 20 (FIG. 1), e.g., on the dissector portion 83 or tip 85 in the embodiment shown in FIG. 16. To establish, and maintain, connection with the end effector 20, it is envisioned that the attachment structure 306 included at the proximal end 302 of the introducer member 300 may be formed from a material different than that comprising the remainder of the introducer member 300. In one specific embodiment, for example, it is envisioned that the attachment structure 306 may be formed from a material having a higher durometer than that of the material comprising the remainder of the introducer member 300.

With continued reference to FIGS. 13-15, in one embodiment of the present disclosure, the attachment structure 306 (FIGS. 13, 14) and the engagement structure 82 (FIG. 15) are configured and dimensioned for engagement in a snap-fit manner. More specifically, the attachment structure 306 includes one or more raised protrusions 308 that extend inwardly into the hollow 304, and the engagement structure 82 includes one or more recess(es) 84 that correspond in configuration and dimensions to the protrusion(s) 308. It is contemplated that the particular configuration and dimensions of the protrusion(s) 308 and the recess(es) 84 may be such that the clinician is provided with an audible, or tactile, indication upon successful connection of the introducer member 100 with the end effector 20.

Figure 17:
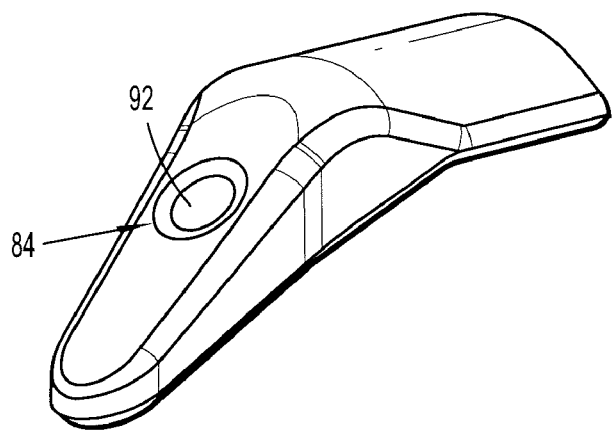
FIG. 17 is a top, perspective view illustrating an alternative embodiment of the dissector portion for use with the introducer member shown in FIG. 16.

The protrusion(s) 308 and the recess(es) 84 may have any geometrical configuration suitable for the intended purpose of establishing a releasable connection between the introducer member 300 and the end effector 20 (FIG. 1). For example, it is contemplated that the protrusion(s) 308 may be configured as one or more raised ribs 310 (FIG. 13), and that the recess(es) 84 may be configured as one or more corresponding linear channels 85 (FIG. 15). Alternatively, the protrusion(s) 308 may be configured as one or more hemispherical protuberances 312 (FIG. 16), and the recess(es) 84 may be configured as one or more corresponding cavities 92 (FIG. 17).

Referring now to FIGS. 1 and 13-15, a method of fastening tissue with the surgical fastener applying apparatus 10 (FIG. 1) will be discussed in connection with the introducer member 300. Prior to inserting the surgical fastener applying apparatus 10 (FIG. 1) into the patient, the introducer member 300 (FIGS. 14, 15) is connected to the end effector 20 (FIG. 1), e.g., to the dissector portion 83 (FIGS. 1, 3, 16) of the anvil component 28 (FIG. 3). Upon connection, the attachment structure 306 (FIGS. 14, 15) included at the proximal end 302 of the introducer member 300 mates with the corresponding engagement structure 82 (FIG. 16) included on the dissector portion 83 (FIG. 16), or other component of the end effector 20.

Following assembly, the surgical fastener applying apparatus 10 (FIG. 1) is inserted into, and advanced distally through, the patient's tissue. During distal advancement, the introducer member 300 atraumatically separates the patient's internal tissues and organs to provide the clinician with access to the target tissue "T" (FIG. 9). When the target tissue "T" is reached, the clinician may elect to remove the introducer member 300, e.g., through an incision, or alternatively, the introducer member 300 may be left in place. When left in place, the flexible material comprising the introducer member 300 allows the introducer member 300 to bend and flex during manipulation to accommodate movement of the introducer member 300 without damaging the patient's internal tissues. The clinician then orients the surgical fastener applying apparatus 10 (FIG. 1) such that the target tissue "T" (FIG. 9) is disposed between the open jaws 24, 26 (FIG. 1) of the end effector 20. After the target tissue "T" is positioned as desired, the jaws 24, 26 are approximated using the handle assembly 12 to clamp the target tissue "T" therebetween, and the surgical fastener applying apparatus 10 is fired to thereby eject the surgical fasteners 36 (FIG. 2) from the surgical fastener cartridge 34, as discussed above. After passing through the target tissue "T," the surgical fasteners 36 are formed through engagement with the anvil plate 30 to achieve a formed configuration, and thereby attach adjacent portions of the target tissue "T." During ejection of the surgical fasteners 36 from the surgical fastener cartridge 34, the target tissue "T" is simultaneously, or nearly simultaneously, severed by the aforementioned knife 52 (FIG. 2) which moves in concert with the drive beam 78 in a position behind, i.e., proximally of, the sled 76.

Referring now to FIGS. 18 and 19, in an alternative embodiment of the present disclosure, a connector member 400 is provided to connect the surgical fastener applying apparatus 10 (FIG. 1), e.g., the anvil component 28, with the introducer member 300 discussed in connection with FIGS. 14 and 15.

The connector member 400 is formed from a biocompatible material suitable for contact with a patient's internal tissue during a surgical procedure, e.g., polymeric materials or stainless steel, and includes respective proximal and distal ends 402, 404. The connector member 400 is configured and dimensioned for releasable engagement with the anvil component 28, or other such component of the end effector 20, as well as the introducer member 300, to facilitate operative attachment of the introducer member 300 to the end effector 20. Specifically, the proximal end 402 of the connector member 400 is engagable with the end effector 20, (FIG. 1), e.g., the dissector portion 83 of the anvil component 28, as shown in FIGS. 18 and 19, such that the connector member 400 extends distally from the anvil component 28, and the distal end 404 of the connector member 400 is engagable with the proximal end 302 of the introducer member 300, such that the introducer member 300 extends distally from the connector member 400.

As seen in FIG. 19, in one embodiment of the connector member 400, the proximal end 402 thereof includes an internal space 406 that is configured and dimensioned to at least partially receive the dissector portion 83 of the anvil component 28. To facilitate connection between the connector member 400 and the anvil component 28, the proximal end 402 of the connector member 400 includes proximal attachment structure 408 that is configured and dimensioned for releasable connection with the aforedescribed engagement structure 82 included on the dissector portion 83, which corresponds in configuration and dimensions thereto. Although illustrated as part of the dissector portion 83 in FIGS. 18 and 19, as discussed above, it should be appreciated that the engagement structure 82 may be associated with any other portion of the anvil component 28 (or the surgical fastener cartridge 34 (FIG. 2), in alternative embodiments of the present disclosure).

In the embodiment of the connector member 400 shown in FIGS. 18 and 19, the proximal attachment structure 408 is illustrated as including one or more raised protrusions 410 extending inwardly into the internal space 406 that is/are configured and dimensioned for engagement with the recess(es) 84 formed on the dissector portion 83 of the anvil component 28. In alternative embodiments of the present disclosure, however, the proximal attachment structure 408 and the engagement structure 82 may assume any configuration or dimensions suitable for the intended purpose of creating a releasable connection between the connector member 400 and the end effector 20 (FIG. 1). As discussed above with respect to the introducer member 100 (FIGS. 1-11), it is contemplated that the particular configuration and dimensions of the attachment structure 408 and the engagement structure 32 may be such that the clinician is provided with an audible, or tactile, indication upon successful connection of the connector member 400 to the end effector 20.

To facilitate engagement between the connector member 400 and the introducer member 100, the distal end 404 of the connector member 400 includes distal attachment structure 412 that is configured and dimensioned for partial or complete reception by the hollow 304 (FIG. 19) included at the proximal end 302 of the introducer member 300.

In one embodiment, it is envisioned that the distal attachment structure 412 may include one or more protrusions (not shown), e.g., having an annular configuration, that are configured and dimensioned for engagement with one or more recesses (not shown) formed in the hollow 304 at the proximal end 302 of the introducer member 300 such that the distal attachment structure 412 is engagable with the proximal end 302 of the introducer member 300 in a snap-fit, or friction-fit, arrangement. As mentioned in connection with the attachment structure 408 formed at the proximal end 402 of the connector member and the engagement structure 82 formed on the end effector 20 (FIG. 1), the distal attachment structure 412 and the hollow 304 may be configured and dimensioned so as to provide the clinician with an audible, or tactile, indication upon successful connection of the connector member 400 to the introducer member 300.

Alternatively, however, as seen in FIGS. 18 and 19, the distal attachment structure 412 may include a series of tapered portions 414 that progressively decrease in size to define ridges 416 at the location where adjacent tapered portions 414 intersect. In this embodiment, as the distal attachment structure 412 is received by the hollow 304, the flexible material comprising the introducer member 300 allows the tapered portions 414 to expand the proximal end 302 of the introducer member 300 outwardly such that an interference fit is created between the proximal end 302 of the introducer member and the distal attachment structure 412 of the connector member 400. After expansion, the ridges 416 engage the inner surface of the hollow 304 in a manner which maintains the position of the introducer 300 relative to the connector member 400 until disconnection is desired.

Referring now to FIGS. 1, 18, and 19, a method of fastening tissue with the surgical fastener applying apparatus 10 (FIG. 1) will be discussed in connection with the introducer member 300 and the connector member 400. Prior to inserting the surgical fastener applying apparatus 10 (FIG. 1) into the patient's tissue, the proximal end 402 of the connector member 400 is attached to the end effector 20, e.g., the dissector portion 83 of the anvil component 28, and the introducer member 300 is connected to the distal end 404 of the connector member 400. Upon connection, the proximal attachment structure 408 of the connector member 400 mates with the corresponding engagement structure 82 included on the dissector portion 83, and the distal attachment structure 412 of the connector member 400 is inserted into the hollow 304 defined in the proximal end 302 of the introducer member 300 such that the ridges 416 engage an inner surface thereof to maintain the relative positions of the introducer member 300 and the connector member 400.

After assembly, the surgical fastener applying apparatus 10 (FIG. 1) is inserted into, and advanced distally through, the patient's tissue, during which time the introducer member 300 atraumatically separates the target tissue "T" (FIG. 9) from any collateral tissue "C" to provide access to the target tissue "T" with the surgical fastener applying apparatus 10.

When the target tissue "T" is reached, the clinician may elect to remove the introducer member 300 and the connector member 400, or leave them in place, as mentioned previously. The clinician can then proceed with the grasping, fastening, and cutting of the target tissue "T" in accordance with the discussion above.

Figure 20:
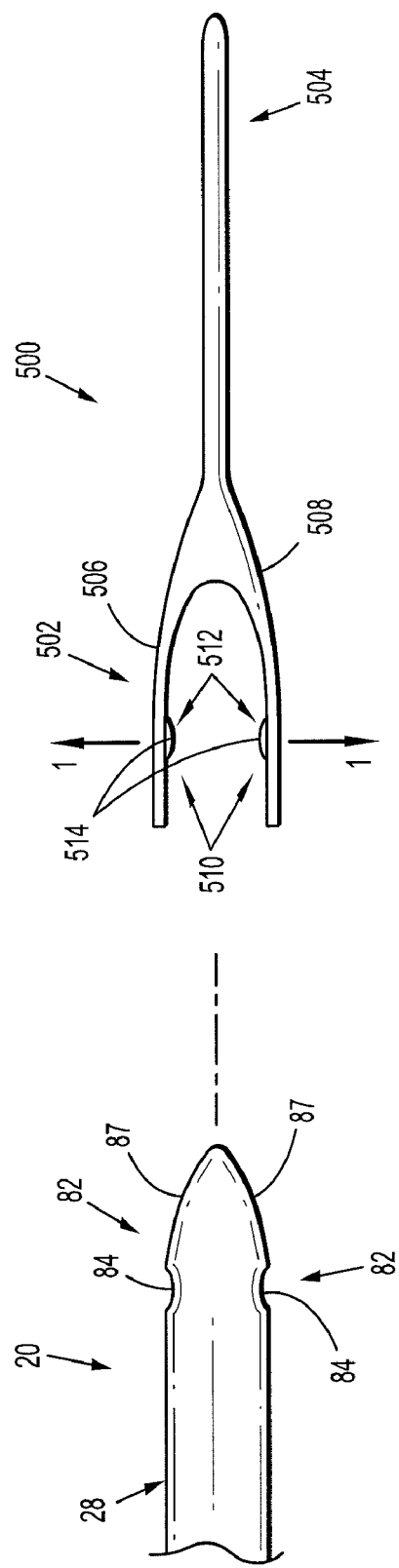
FIG. 20 is a partial, top, plan view illustrating another embodiment of the presently disclosed introducer member shown separated from the end effector according to an embodiment of the present disclosure.

Referring now to FIG. 20, another embodiment of the presently disclosed introducer member, which is identified by the reference character 500, will be discussed. The introducer 500 includes a proximal end 502 and a distal end 504. The proximal end 502 of the introducer member 500 is formed from an at least partially resilient material, and includes a Y-shaped configuration with respective first and second branches 506, 508. The branches 506, 508 are configured and dimensioned to facilitate releasable engagement with the end effector 20 of the surgical fastener applying apparatus 10 (FIG. 1), e.g., with either the anvil component 28 (FIGS. 2, 3) or the surgical fastener cartridge 34 (FIG. 2). Specifically, the branches 506, 508 of the introducer member 500 include attachment structure 510 that is configured and dimensioned for releasable connection with the engagement structure 82 included on the end effector 20. While the engagement structure 82 is shown as formed on the anvil component 28 of the end effector 20 in the illustrated embodiment, it should be appreciated that the attachment structure 510 may alternatively be configured and dimensioned for engagement with structure formed on the surgical fastener cartridge 34 (FIG. 2). Additionally, although the branches 506, 508 of the introducer member 500 are illustrated as being configured and dimensioned to facilitate connection with engagement structure 82 that is positioned on side portions 87 of the end effector 20, in alternative embodiments, it is envisioned that the engagement structure 82 may be included on upper and lower portions of the end effector 20, and that the branches 506, 508 of the introducer member 500 may be configured and dimensioned accordingly.

In the embodiment of the introducer 500 illustrated in FIG. 20, the attachment structure 510 included on the branches 506, 508 includes a pair of protrusions 512 that are configured as arcuate detents 514, and the engagement structure 82 included on the anvil component 28 is configured as recess(es) 84 of corresponding configuration and dimensions. It should be appreciated, however, that in alternative embodiments of the present disclosure, the attachment structure 510 and the engagement structure 82 may assume other geometrical configurations without departing from the scope of the present disclosure.

The distal end 504 of the introducer member 500 includes an elongate profile that is configured and dimensioned to facilitate atraumatic distal advancement of the introducer member 500 through the patient's tissue. The distal end 504 includes a flexible, resilient material that allows the distal end 504 to bend and flex when necessary so as to permit the clinician to navigate the introducer member 500 around the target tissue "T" (FIG. 9) and the collateral tissue "C" without causing unnecessary trauma.

Upon application of the introducer member 500 to the anvil component 28, the attachment structure 510 rides along an outer surface of the end effector 20, which causes the branches 506, 508 to splay slightly outward in the direction indicated by arrows 1. However, upon positioning of the attachment structure 510 within the engagement structure 82, the resilient material comprising the proximal end 502 allows the branches 506, 508 to return to their normal configuration, whereby the branches 506, 508 are caused to engage the end effector 20 in press-fit arrangement. To disconnect the introducer 500 from the end effector 20, the clinician applies a predetermined force to the introducer member 500 to separate the attachment structure 510 from the engagement structure 82. For example, the clinician can pull the introducer member 500 distally, or rotate the introducer member 500 relative to the end effector 20, to force the detents 514 from the recess (es) 84. more In an alternative embodiment of the introducer member 500, which is shown in FIG. 21, it is envisioned that the branches 506, 508 of the introducer member 500 may further include pivot members 516, in addition to the attachment structure 510, to facilitate separation of the introducer 500 from the end effector 20. In this embodiment, when disengagement of the introducer 500 from the end effector 20 is desired, a force is applied to the branches 506, 508 about the pivot members 516 that is directly inwardly, i.e., in the direction identified by arrows 2. This application of force to the branches 506, 508 about the pivot members 516 causes the branches 506, 508 to bend about the pivot members 516 such that more proximal portions of the branches 506, 508 splay outwardly, i.e., in the direction indicated by arrows 1, thereby releasing the attachment structure 510 from the engagement structure 82, and allowing for removal of the introducer member 500.

Referring again to FIG. 20, it is envisioned that the proximal end 502 of the introducer member 500, including the attachment structure 510, may be formed from a first material, whereas the distal end 504 of the introducer member 500 may be formed from a second, different material. For example, the first material may have a higher durometer than the second material. Incorporating a material with a higher durometer at the proximal end 502 of the introducer 500, as opposed to a more compliant material, facilitates a more secure connection between the attachment structure 510 and the engagement structure 82. The material comprising the distal end 504 of the introducer 500, while more flexible than the material comprising the proximal end 502, is sufficiently rigid to facilitate separation of the target tissue "T" (FIG. 9) from the collateral tissue "C" in the manner discussed above.

In one embodiment of the disclosure, it is envisioned that the distal end 504 of the introducer member 500 may incorporate a material having a highly visible color, such as red, green, yellow, etc., in order to increase visibility of the introducer member 500 within an internal workspace.

Figure 22:
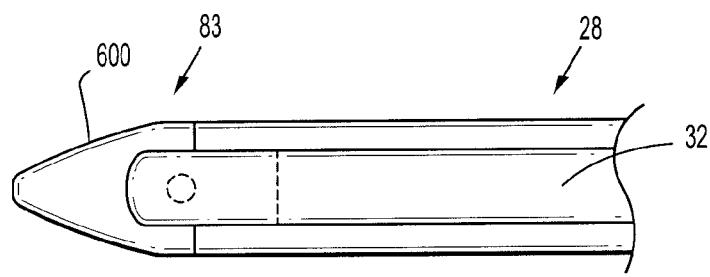
FIG. 22 is a partial, top, schematic view illustrating one embodiment of the dissector portion of the anvil component including a tip that is secured between the anvil plate and the anvil cover.
Figure 23:
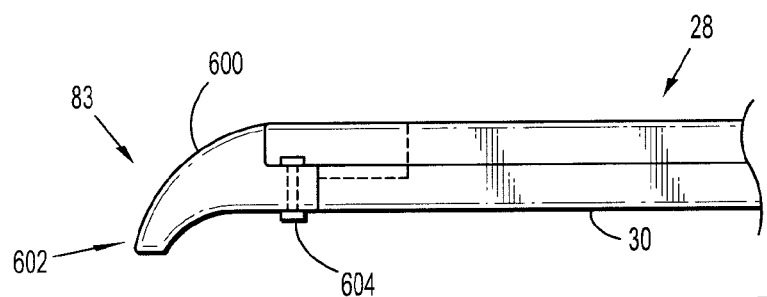
FIG. 23 is a partial, side, schematic view of the dissector portion seen in FIG. 22.
Figure 24:
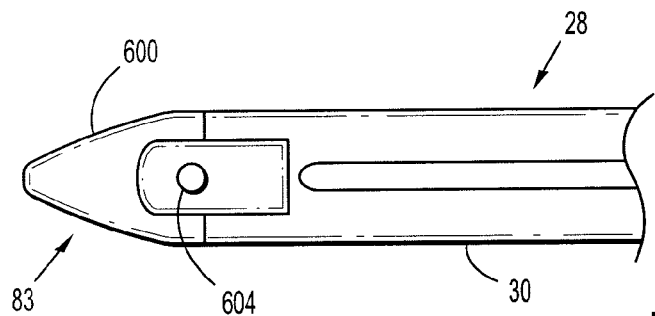
FIG. 24 is a partial, bottom, schematic view of the dissector portion seen in FIG. 22.

Referring now to FIGS. 22-24, in one embodiment of the present disclosure, it is envisioned that the dissector portion 83 of the anvil component 28 may comprise a tip 600 that is secured between the anvil plate 30 (FIGS. 23, 24) and the anvil cover 32 (FIG. 22). As seen in FIG. 23, the tip 600 includes an arcuate distal portion 602 that is configured and dimensioned to facilitate separation of the target tissue "T" (FIG. 9) from any collateral tissue "C." The tip 600 may be formed from any suitable biocompatible material, including but not limited to polymeric materials, through any suitable process, such as molding.

The tip 600 is secured to the anvil plate 30 via a post 604, rivet, or the like, that extends through corresponding openings (not shown) formed in the tip 600 and the anvil plate 30. Following placement of the post 604 through the tip 600 and the anvil plate 30, the anvil cover 32 (FIG. 22) is secured to the anvil plate 30 in the aforedescribed manner, e.g., via one or more welds.

Figure 25:
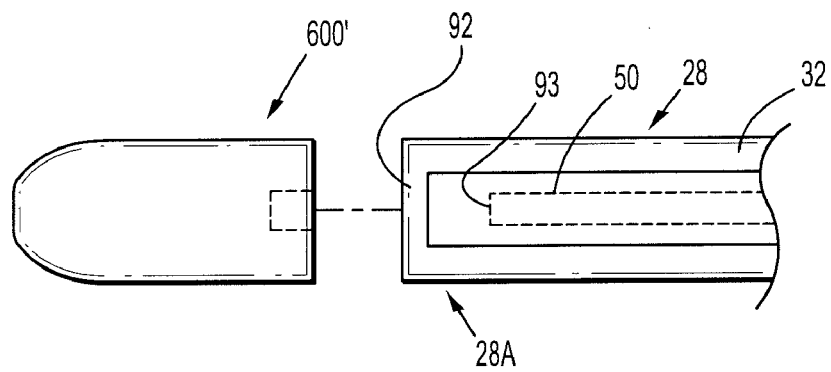
FIG. 25 is a partial, top, schematic view illustrating an alternative embodiment of the tip of the dissector portion shown separated from the remainder of the anvil component.
Figure 26:
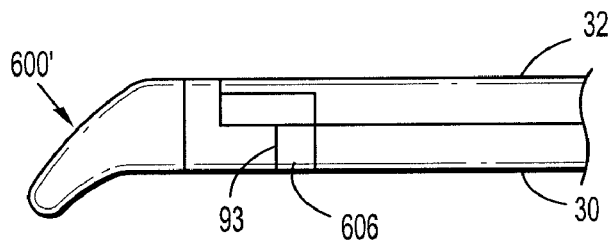
FIG. 26 is a partial, side, schematic view illustrating the tip seen in FIG. 25 following connection with the anvil component.
Figure 27:
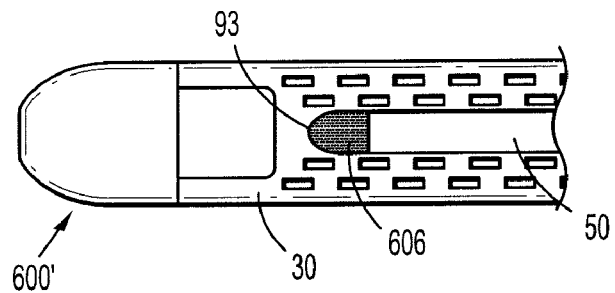
FIG. 27 is a partial, bottom view illustrating the tip seen in FIG. 25 following connection with the anvil component.

Referring now to FIGS. 25-27, an alternative embodiment of the tip, which is identified by the reference character 600', will be discussed. The tip 600' is substantially similar to the tip 600 discussed with respect to FIGS. 22-24, and accordingly, will only be described with respect to any differences therefrom.

The tip 600' is inserted into the anvil component 28 through an opening 92 (FIG. 25) formed in a distal end 28A thereof. As discussed above with respect to the tip 600 (FIGS. 22-24), when properly positioned relative to the anvil component 28, the tip 600' is oriented between the anvil plate 30 (FIGS. 26, 27) and the anvil cover 32 (FIG. 25). In lieu of the post 604 (FIG. 24) discussed above, or in addition thereto, the tip 600' includes a tab 606 that is configured and dimensioned for positioning within the slot 50 formed in the anvil plate 30 to inhibit inadvertent disconnection of the tip 600' from the anvil component 28. Specifically, the tab 606 is configured and dimensioned for engagement with a distal wall 93 (FIGS. 25, 26) defined by the slot 50. Engagement of the tab 606 and the distal wall 93 of the slot 50 prevents distal movement of the tip 600' relative to the anvil component 28 beyond a predetermined location.

Figure 28:
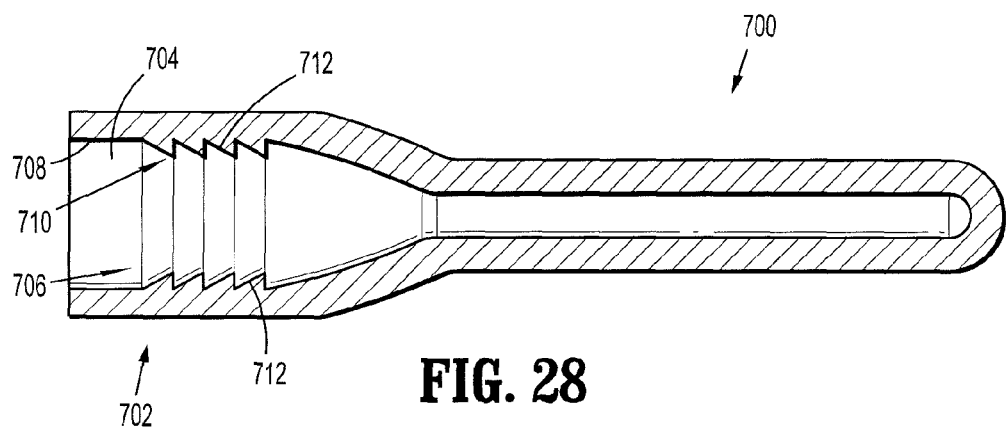
FIG. 28 is a longitudinal, cross-sectional view of another embodiment of the presently disclosed introducer member.

To further facilitate separation of the target tissue "T" (FIG. 9) from any collateral tissue "C," it is envisioned that the tip 600 (FIGS. 22-24), 600' (FIGS. 25-27) may be used in conjunction with any embodiment of the presently disclosed introducer member described herein, such as, for example, the introducer member identified by the reference character 700 in FIG. 28.

The introducer member 700 includes a proximal end 702 defining a hollow 704 that is configured and dimensioned to facilitate attachment with the distal end 28A of the anvil component 28 (see FIG. 25). It should be appreciated, however, that the hollow 704 may be configured and dimensioned for engagement with the surgical fastener cartridge 34 (FIG. 2) in alternative embodiments of the introducer member 700. To facilitate attachment of the introducer member 700 to the anvil component 28, the introducer member 700 includes attachment structure 706 that is positioned on an internal wall 708 of the proximal end 702. The attachment structure 706 extends into the hollow 704, and includes a plurality of protrusions 710. Although the protrusions 710 are illustrated as including a configuration defining a plurality of teeth 712, it should be appreciated that alternative configurations for the protrusions 710 are not beyond the scope of the present disclosure, e.g., protrusions with an arcuate configuration.

Figure 29:
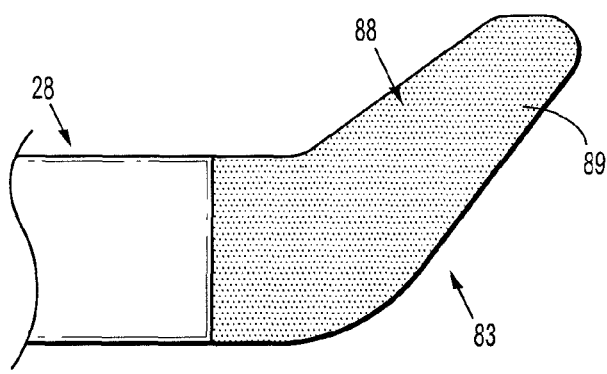
FIG. 29 is a partial, side, plan view illustrating another embodiment of the dissector portion of the anvil component incorporating a roughened surface.

To further enhance the connection between the introducer member 700 and the anvil component 28, it is contemplated that the anvil component 28, e.g., the dissector portion 83, may include a roughened surface 88. While the roughened surface 88 has been illustrated as formed on the anvil component 28 in the illustrated embodiment, the roughened surface 88 alternatively be formed on the surgical fastener cartridge 34 (FIG. 2) in order to enhance the connection between the introducer member 700 and the surgical fastener cartridge 34, when desired. The roughened surface 88 may include any structure suitable for the intended purpose of facilitating attachment with the proximal end 702 (FIG. 28) of the introducer member 700. For example, the roughened surface 88 may include a surface coating 89, as shown in FIG. 29, or alternatively, the roughened surface 88 may include a glass-bit surface finish 90, as shown in FIG. 30.

Figure 30:
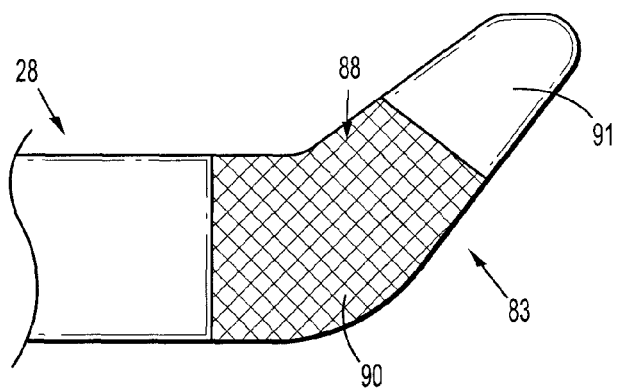
FIG. 30 is a partial, side, plan view illustrating an alternative embodiment of the dissector portion shown in FIG. 29.

To facilitate insertion of the anvil component 28 into the hollow 704 defined in the proximal end 702 of the introducer member 700, it is envisioned that the anvil component 28 may include a polished tip 91, as also shown in FIG. 30. The polished tip 91 serves to reduce friction between the anvil component 28 and the proximal end 702 of the introducer member 700 in order to allow for sufficient advancement of the anvil component 28 into the hollow 704 to facilitate engagement of the attachment structure 706 with the roughened surface 88.

Figure 31:
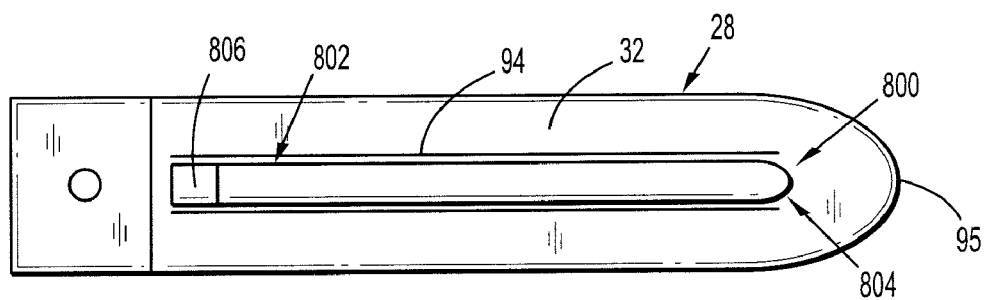
FIG. 31 is a partial, top view of the anvil component including an alternative embodiment of the presently disclosed introducer member.
Figure 32:
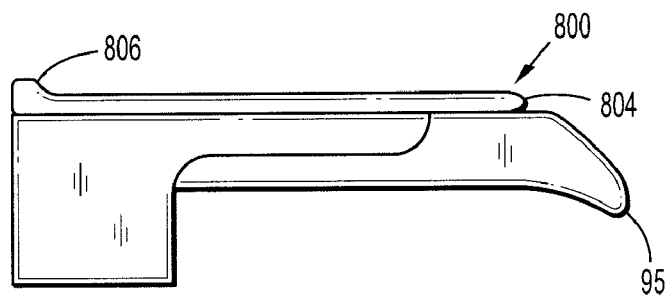
FIG. 32 is a partial, side view of the anvil component shown in FIG. 32 illustrating the introducer member in a retracted position.
Figure 33:
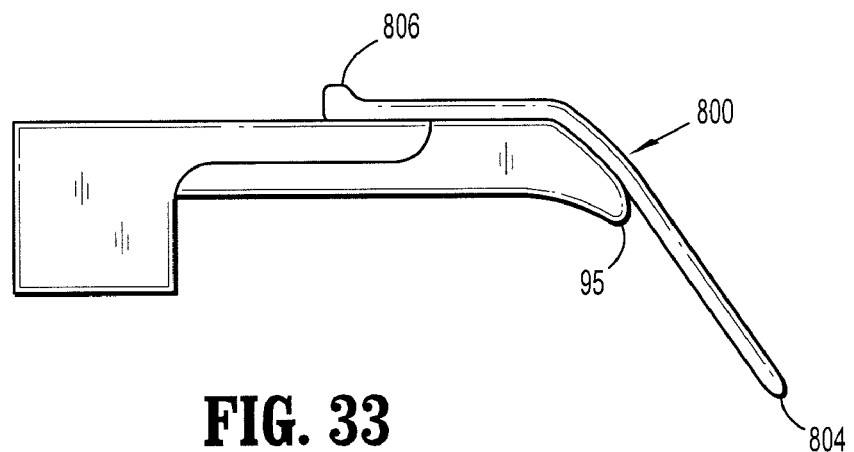
FIG. 33 is a partial, side view of the anvil component shown in FIG. 32 illustrating the introducer member in an advanced position.

With reference now to FIGS. 31-33, an embodiment of the presently disclosed introducer member is illustrated, which is identified by the reference character 800. The introducer member 800 includes a proximal end 802 and a distal end 804, and is configured and dimensioned for longitudinal movement relative to the end effector 20 (FIG. 1), e.g., the anvil component 28. More specifically, the introducer member 800 is configured and dimensioned for slidable movement through a slot 94 formed in the anvil cover 32 such that the introducer member 800 is selectively repositionable between a retracted position (FIGS. 31, 32) and an advanced position (FIG. 33). In the retracted position, the distal end 804 of the introducer member 800 is positioned proximally of a distal-most tip 95 of the anvil component 28, and in the advanced position, the distal end 804 of the introducer member 800 is positioned distally of the distal-most tip 95 of the anvil component 28 to facilitate separation of the target tissue "T" (FIG. 9) from any collateral tissue "C."

To facilitate movement between the retracted and advanced positions, it is envisioned that the introducer member 800 may include a manual member 806 that is configured and dimensioned for engagement by the clinician. In one embodiment of the introducer member 800, the manual member 806 extends upwardly from the introducer member 800, and may be positioned at the proximal end 802 of the introducer member 800, as shown in FIGS. 31-33, or in any other suitable location. Alternatively, the manual member 806 may constitute a roughened surface (not shown) which does not extend upwardly from the introducer member 800, but rather, extends along the plane of the anvil cover 32 (FIG. 3).

Figure 34:
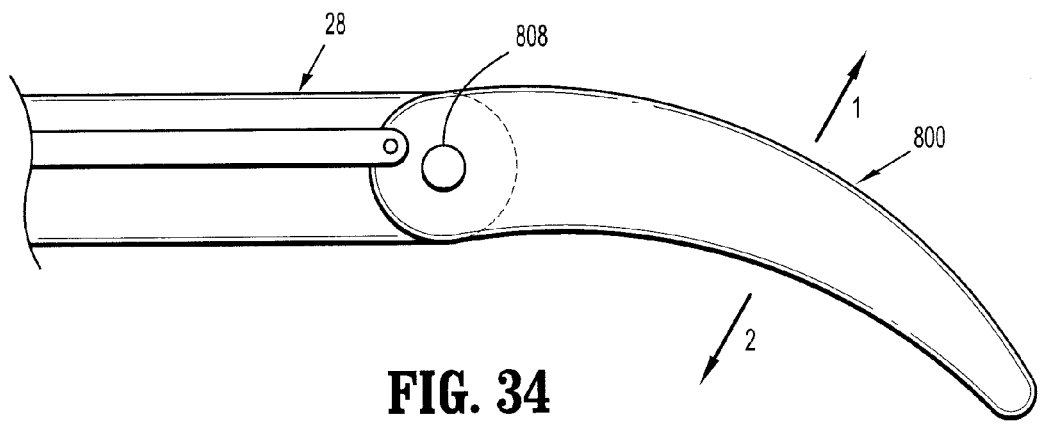
FIGS. 34 and 35 are partial, top views of the anvil component including an another embodiment of the presently disclosed introducer member that is pivotably connected thereto.
Figure 35:
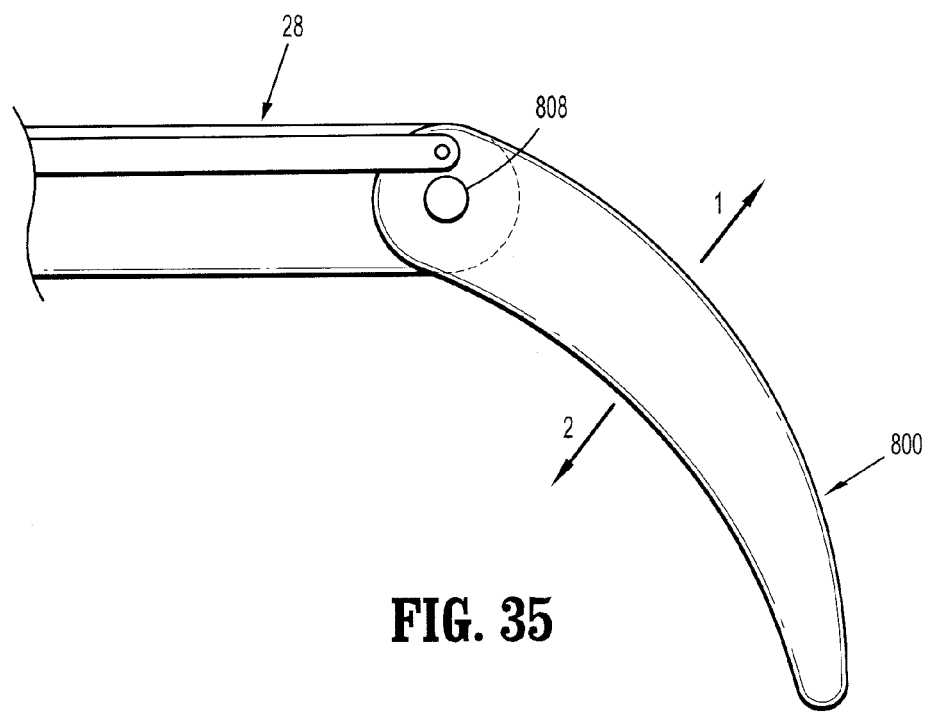

In order to increase the clinician's ability to manipulate the introducer member 800, it is envisioned that the introducer member 800 may be connected to the end effector 20 (FIG. 1) so as to allow for lateral movement thereof, e.g., side-to-side, as well as longitudinal movement. For example, as shown in FIGS. 34 and 35, the introducer member 800 may be connected to the anvil component 28 via a pivot member 808 such that the introducer member 800 is movable in the directions indicated by arrows 1 and 2. Allowing for both longitudinal and lateral movement provides the clinician with increased access to internal spaces, which allows the clinician to more accurate place the introducer member 800 during navigation around the patient's internal tissues.

Figure 36:
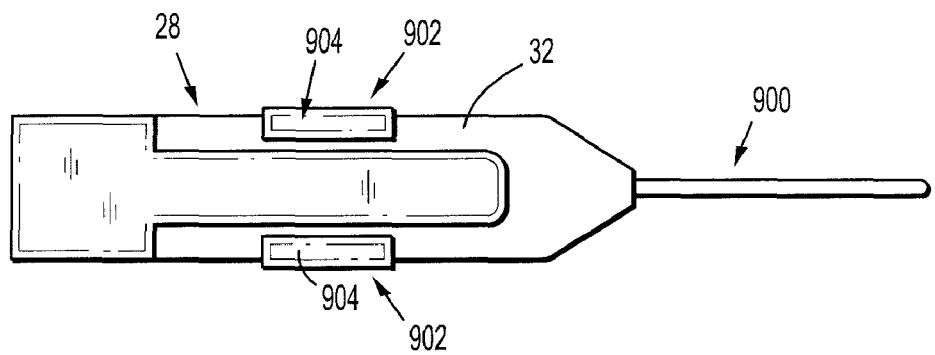
FIG. 36 is a partial, top view of the anvil component including an alternative embodiment of the presently disclosed introducer member.
Figure 37:
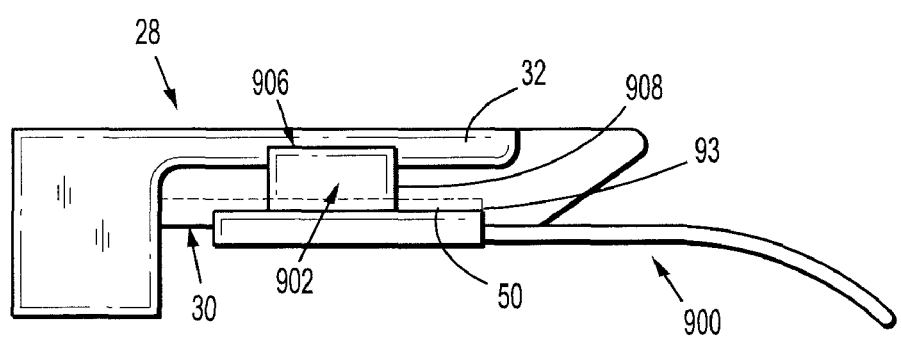
FIG. 37 is a partial, side, schematic view of the anvil component and the introducer member shown in FIG. 36.
Figure 38:
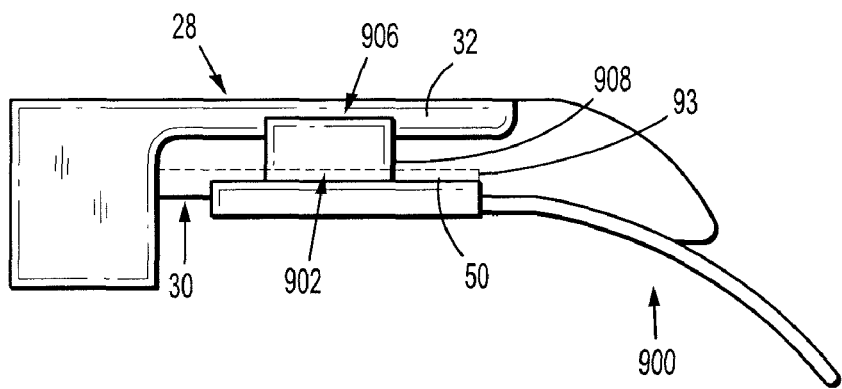
FIG. 38 is a partial, side, schematic view of an alternative embodiment of the anvil component and the introducer member shown in FIG. 36.

FIGS. 36-38 illustrate another embodiment of the introducer member, which is identified by the reference character 900. The introducer member 900 includes a pair of flexible wings 902 with feet 904 that are configured and dimensioned to securely engage the anvil component 28, e.g., the anvil cover 32. For example, it is envisioned that the feet 904 may be configured and dimensioned to engage the anvil component 28 in snap-fit relation. The introducer member 900 further includes a rail 906 (FIGS. 37, 38) that is configured and dimensioned for positioning within the slot 50 formed in the anvil plate 30. The rail 906 includes a wall 908 that is configured and dimensioned for engagement with the distal wall 93 defined by the slot 50 to inhibit distal movement of the introducer member 900 relative to the anvil component 28 beyond a predetermined location in order to reduce the likelihood of inadvertent disconnection therefrom. After the anvil component 28 is in the desired position adjacent the target tissue "T" (FIG. 9), prior to firing of the surgical fastener applying apparatus 10 (FIG. 1), the introducer member 900 can be removed from the anvil component 28 by disengaging the feet 904 from the anvil cover 32. For example, the wings 902 can be deformed laterally outward, e.g., by rotating the introducer member 900 relative to the anvil component 28.

FIGS. 39 and 40 illustrate another embodiment of the presently disclosed introducer that is identified by the reference character 1000. The introducer member 1000 is mounted to the anvil component 28 by a pivot member 1002 that extends through the introducer 1000 and one or more pivot plates 1004 that are secured to an outer surface of the end effector 20. The pivot member 1002 may be any member suitable for the intended purpose of facilitating lateral pivotal movement of the introducer member 1000, i.e., side-to-side in the direction indicated by arrows 1 (FIG. 39), including but not limited to screws, rivets, or the like.

It is envisioned that the introducer member 1000 may be utilized in connection with end effectors 20 of various configurations. For example, it is envisioned that the introducer member 1000 may be employed in connection with an anvil component 28 having a substantially linear configuration (see FIG. 41), or alternatively, with an anvil component 28 that includes the aforementioned dissector portion 83, as shown in FIG. 40.

Another embodiment of the introducer member, which is identified by the reference character 1100, is illustrated in FIGS. 41 and 42. The introducer member 1100 includes a proximal end 1102 with a collar 1104 that is configured and dimensioned for positioning about the anvil cover 32, and a distal portion 1106 that is configured and dimensioned to facilitate separation of the target tissue "T" (FIG. 9) from any collateral tissue "C." The collar 1104 is configured and dimensioned to engage the anvil component 28 such that relative longitudinal movement therebetween is substantially inhibited. For example, it is envisioned that the collar 1104 may comprise an at least partially resilient material allowing the collar 1104 to be deformed outwardly upon association with the anvil component 28 in order to facilitate a snap-fit connection with the anvil cover 32.

To further enhance stability of the connection between the introducer 1100 and the anvil component 28, it is envisioned that the distal portion 1106 of the introducer member 1100 may include one or more tabs 1108, snaps, protrusions, or the like that are configured and dimensioned for engagement with corresponding structure in the anvil cover 32, as shown in FIG. 41.

With reference now to FIG. 43, another embodiment of the introducer member, which is identified by the reference character 1200, will be discussed. The introducer member 1200 includes a proximal end 1202 incorporating attachment structure 11204, a distal end 1206 including an atraumatic tip portion 1208, and an elongate body portion 1210. As illustrated in FIG. 43, the elongate body portion 1210 of the introducer member 1200 may include a tapered configuration to facilitate separation of the target tissue "T" (FIG. 9) from any collateral tissue "C."

The proximal end 1202 of the introducer member 1200 is configured and dimensioned for insertion into the opening 92 formed at the distal end 28A of the anvil component 28 such that the introducer member 1200 is positionable between the anvil cover 32 (FIG. 3) and the anvil plate 30. To facilitate attachment of the introducer member 1200 to the anvil component 28, it is envisioned that the proximal end 1202 of the introducer member 1200 and the distal end 28A of the anvil component 28 may include corresponding structure that is configured and dimensioned for mating engagement. For example, in the embodiment shown in FIG. 43, it is envisioned that the attachment structure 1204 included at the proximal end 1202 of the introducer member 1200 may be configured and dimensioned for connection with corresponding engagement structure 96 formed within the opening 92 at the distal end 28A of the anvil component 28 in a press-fit arrangement. In the illustrated embodiment, the attachment structure 1204 is depicted as including a plurality of protrusions 1212, and the engagement structure 96 is depicted as including recesses 97 of corresponding configuration and dimensions. It should be appreciated, however, that alternative configurations for the attachment structure 1204 and the engagement structure 96 are not beyond the scope of the present disclosure.

Although the introducer member 1200 is illustrated as including a configuration similar to that of the dissector portion 83 (FIGS. 1, 3, 15), in alternative embodiments of the present disclosure, it is envisioned that the introducer member 1200 may assume other configurations. For example, as seen in FIG. 43A, the introducer member 1200 may include a more elongate configuration similar to that of the introducer member 100 discussed above with respect to FIGS. 1-10.

Figure 44:
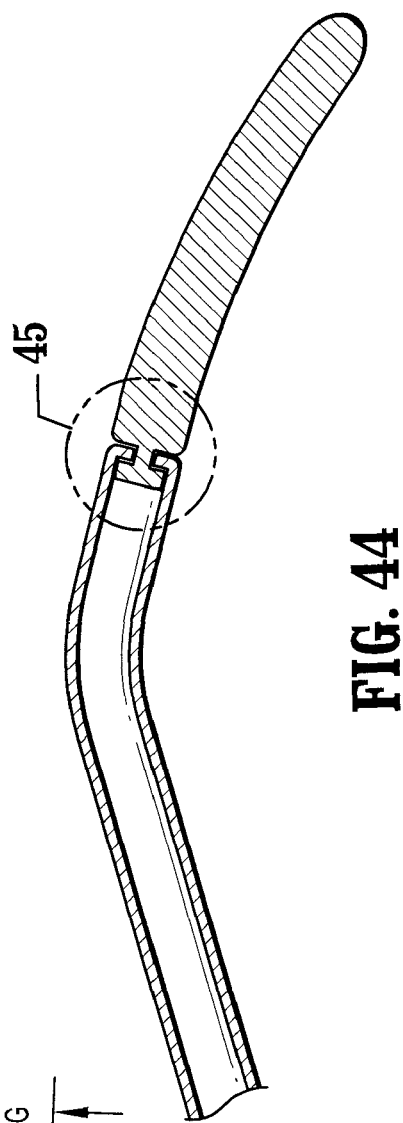
FIG. 44 is a partial, longitudinal, cross-sectional view of the presently disclosed anvil component and introducer member according to another embodiment of the present disclosure.
Figure 45:
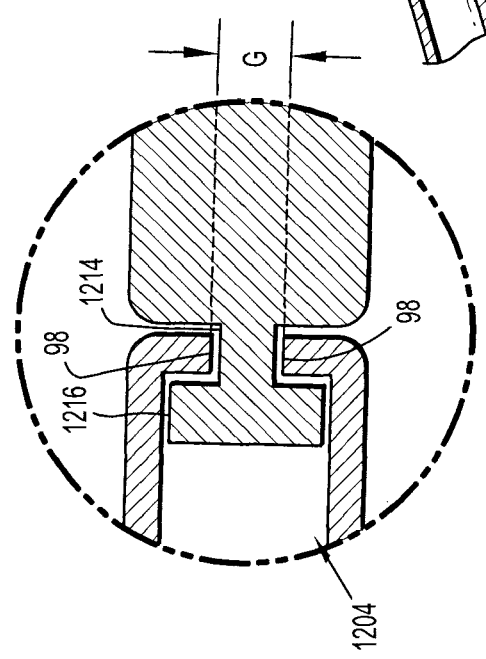
FIG. 45 is an enlarged view of the area of detail indicated in FIG. 44.

Referring now to FIG. 44, in one embodiment, the attachment structure 1204 included at the proximal end 1202 of the introducer member 1200 may include a stem 1214 with a head portion 1216 attached thereto that is configured and dimensioned for positioning within the opening 92 (FIG. 43) formed at the distal end 28A of the anvil component 28. To facilitate retention of the attachment structure 1204 within the opening 92, the engagement structure 96 included at the distal end 28A of the anvil component 28 may include a pair of shoulders 98 defining a gap "G" (FIG. 45) therebetween. The transverse dimension of the gap "G" is larger than the transverse dimension of the stem 1214, but smaller than the transverse dimension of the head portion 1216, in order to prevent inadvertent disconnection of the introducer member 1200 from the anvil component 28.

To facilitate advancement of, and control over, the introducer member 1200 during manipulation within an internal workspace, it is envisioned that the distal end 28A of the anvil component 28 may be formed from a first material, e.g., a rigid material, such as solid or sheet metal, and that the introducer member 1200 may be formed from a second, more flexible material, such as plastic or rubber. To further enhance stability of the connection between the introducer member 1200 and the anvil component 28, it is envisioned that the attachment structure 1204 included at the proximal end 1202 of the introducer member 1200 may be heat-staked to the distal end 28A of the anvil component 28.

Figure 46:
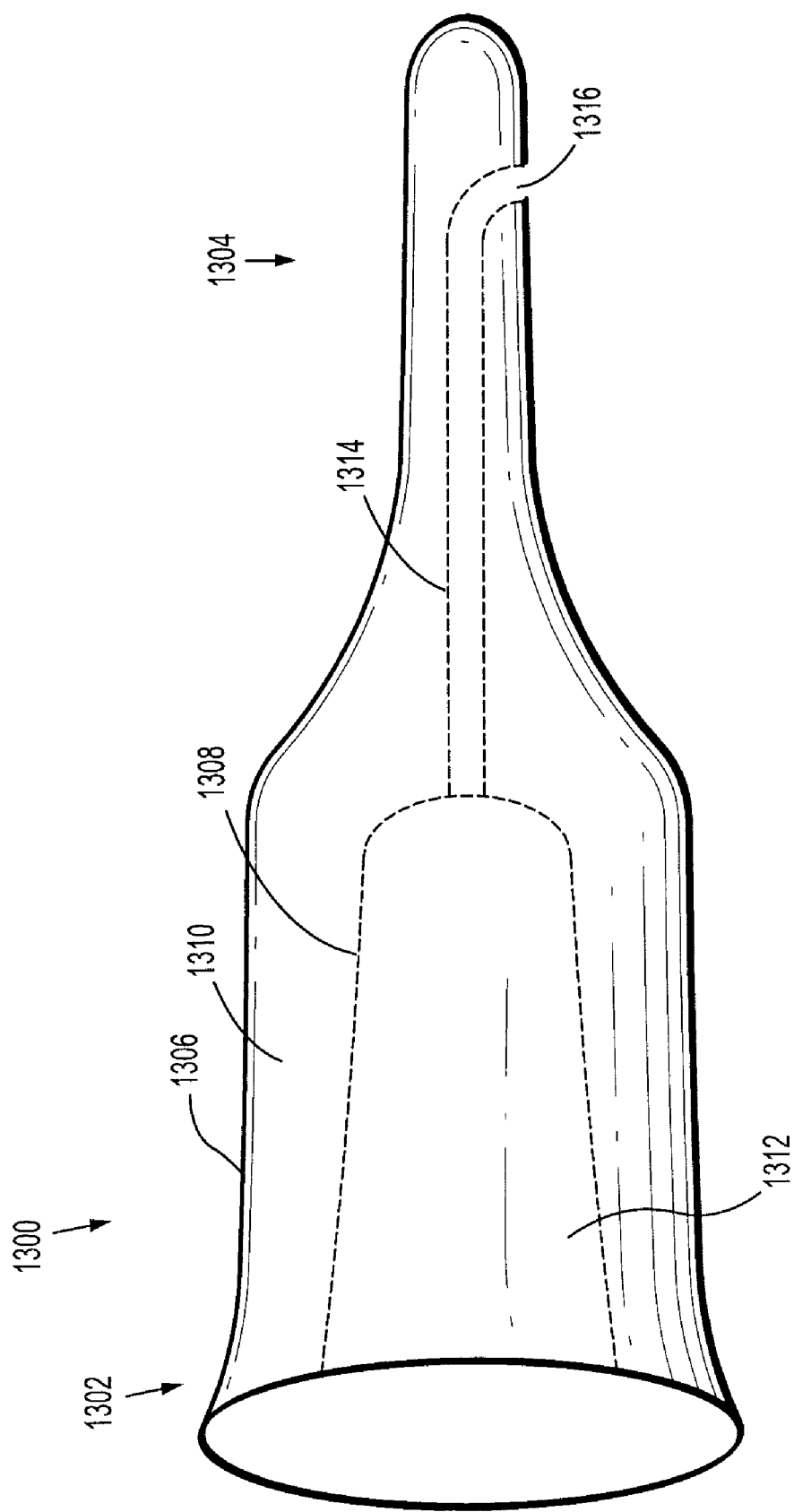
FIG. 46 is a side, schematic view of another embodiment of the presently disclosed introducer member.

FIG. 46 illustrates another embodiment of the presently disclosed introducer member, which is identified by the reference character 1300, that includes a proximal portion 1302 and a distal portion 1304. The proximal portion 1302 of the introducer member 1300 includes an outer layer 1306 and an inner layer 1308 which collectively define a cavity 1310 therebetween, as well as a hollow 1312 that is configured and dimensioned to receive the end effector 20 (FIG. 1), e.g., the anvil component 28 (FIG. 2, 3) or the surgical fastener cartridge 34 (FIG. 2). The introducer member 1300 further includes a passage 1314 extending longitudinally therethrough that is in fluid communication with the cavity 1310 and a port 1316 included on the distal portion 1304 of the introducer member 1300. The passage 1314 allows for the communication of a fluid, such as air or saline, through the port 1316 and into the cavity 1310 to thereby fill and inflate the cavity 1310. It is envisioned that the port 1316 may include a seal (not shown), valve, or the like to inhibit the escape of fluid from the cavity 1310 and/or the port 1316 until such time that deflation of the cavity 1310 is desired.

Prior to inflation of the cavity 1310, the hollow 1312 at the proximal end 1302 of the introducer member 1300 defines a transverse dimension that is smaller than the transverse dimension defined by the component of the end effector 20 to which the introducer member 1300 is to be attached, e.g., a transverse dimension that is smaller than that of the anvil component 28 or the surgical fastener cartridge 34. However, upon inflation of the cavity 1310, as the cavity 1310 fills with fluid, the transverse dimension of the hollow 1312 is increased such that the end effector 20, or component thereof, is positionable within the hollow 1312. Following connection of the proximal end 1302 of the introducer member 1300 to the end effector 20, the clinician can optionally deflate the cavity 1310 by draining the inflation fluid. It is also contemplated herein that the fluid within the cavity 1310 may exert pressure upon the outer layer 1306 and the inner layer 1308, and that this pressure may be transmitted to an outer surface of the end effector 20 (FIG. 1), thus assisting in retention of the proximal portion 1302 of the introducer member 1300 about the end effector 20.

In order to accommodate expansion and contraction of the cavity 1310, it is envisioned that either or both of the outer layer 1306 and the inner layer 1308 comprising the proximal portion 1302 of the introducer member 1300 may be formed from a resilient material, e.g., materials with a relatively low durometer, such as shrink tubing.

Figure 47:
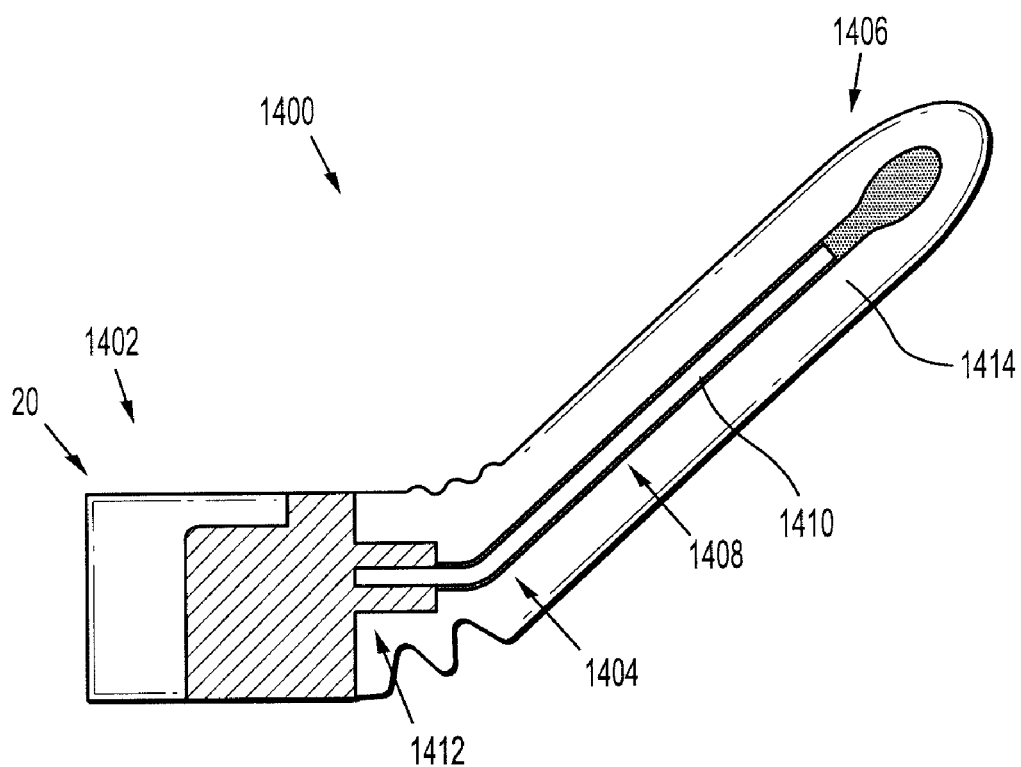
FIG. 47 is a partial, top, cross-sectional view illustrating another embodiment of the presently disclosed introducer member.
Figure 48:
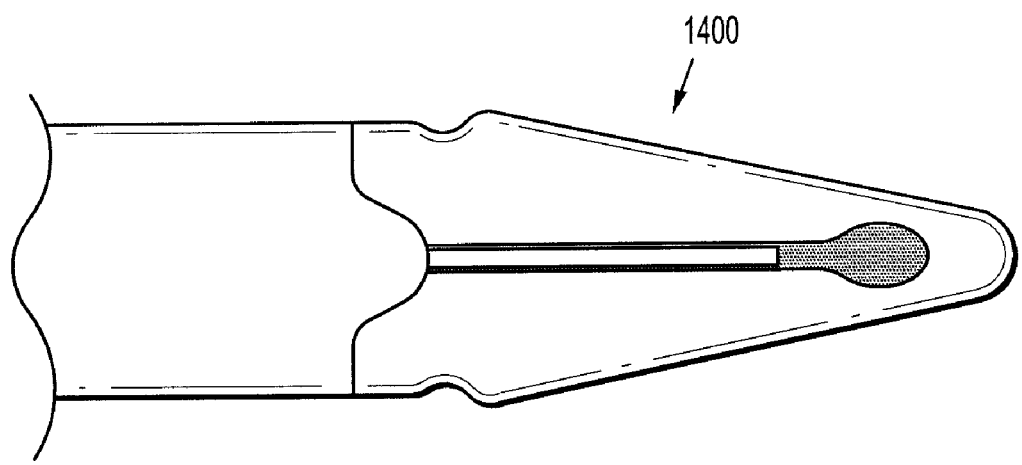
FIG. 48 is a partial, top, cross-sectional view illustrating an alternative embodiment of the introducer member seen in FIG. 47.

FIG. 47 illustrates another embodiment of the presently disclosed introducer member, which is identified by the reference character 1400. The introducer member 1400 includes a proximal portion 1402 including a selectively deformable section 1404, and a distal portion 1406 that is positionable about the deformable section 1404.

The deformable section 1404 includes a resilient member 1408 that is formed from a deformable, e.g., malleable, material that can be manually reconfigured by the clinician in order to assume a desired geometrical configuration. For example, it is envisioned that the resilient member 1408 may include a flexible shaft 1410 that is connected, either directly or operatively, to the end effector 20, as shown in FIG. 47. In the illustrated embodiment the flexible shaft 1410 is connected to the end effector 20 via attachment structure 1412 formed, either integrally or releasably, with the end effector 20, e.g., between the anvil plate 30 (FIG. 3) and the anvil cover 32.

The distal portion 1406 of the introducer member 1400 is formed from a material that is at least partially resilient in order to facilitate atraumatic advancement of the introducer member 1400 during a surgical procedure, such that introducer member 1400 can be effectively navigated about the target tissue "T" (FIG. 9) and any collateral tissue "C" without causing unnecessary trauma. The distal portion 1406 includes an internal cavity 1414 that is configured and dimensioned to receive the deformable section 1404. The distal portion 1406 may be attached to the proximal portion 1402 in any suitable manner, such as, for example, through the incorporation of a resilient material. Incorporating a resilient material allows the distal portion 1406 to be forced over the deformable section 1404 and/or the attachment structure 1412 such that the proximal portion 1402 and the distal portion 1406 engage one another in a force-fit arrangement. Alternatively, it is envisioned that the proximal portion 1402 and the distal portion 1406 may include corresponding structure that is configured and dimensioned for releasable, mating engagement, such as that described in connection with several of the embodiments of the introducer member discussed herein above.

Figure 49:
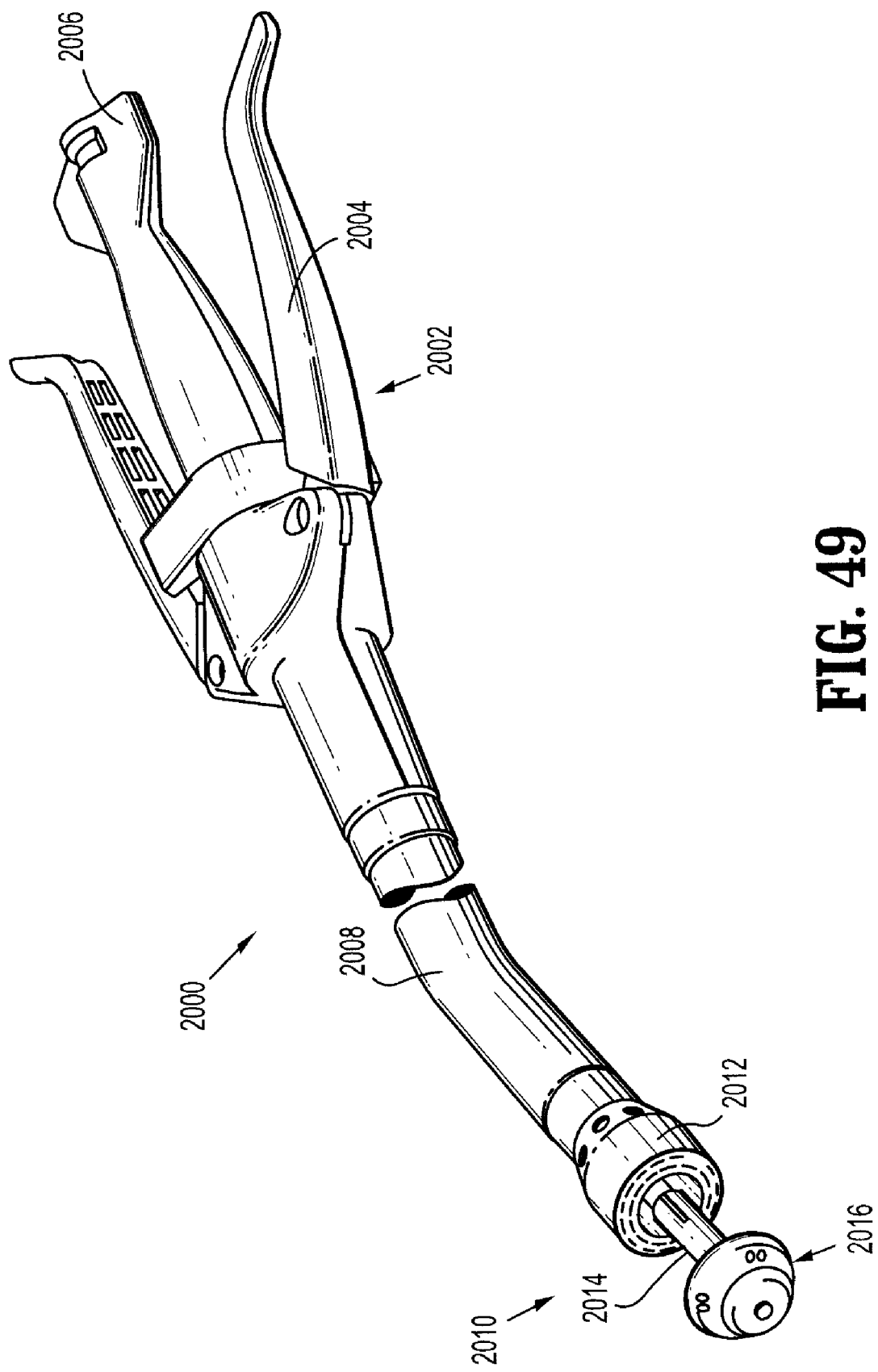
FIG. 49 illustrates an end-to-end anastomosis device for use with an alternative embodiment of the presently disclosed introducer member.

Although the introducer member 1400 is illustrated as including an elongate configuration similar to that of the introducer member 100 discussed above with respect to FIGS. 1-10, in alternative embodiments of the present disclosure, it is envisioned that the introducer member 1400 may assume other configurations. For example, as seen in FIG. 49, the introducer member 1200 may include a configuration similar to that of the dissector portion 83 (FIGS. 1, 3, 15).

While each embodiment of the presently disclosed introducer member has been discussed and illustrated in connection with the end effector 20 (FIG. 1), which is adapted for use in laparoscopic procedures for performing surgical anastomotic fastening of tissue, the introducer member may be adapted for use with any surgical instrument suitable for the intended purpose of applying the plurality of surgical fasteners 36 (FIG. 2) to a section of tissue, and thereafter severing the tissue along a cut-line.

The presently disclosed introducer member may alternatively be adapted for use with a surgical stapling apparatus 3000 (FIG. 49), such as that disclosed in commonly assigned U.S. Pat. No. 7,334,717, currently assigned to Tyco Healthcare Group LP, the contents of which are hereby incorporated by reference herein in its entirety. The surgical stapling apparatus 3000 includes a cartridge receiving half-section 3002, which accommodates a plurality of surgical fasteners, and an anvil half-section 3004. The half-sections 3002, 3004 are pivotally connected via handles 3006, 3008 for approximation during use.

Following approximation of the half-sections 3002, 3004, the surgical fastener applying apparatus 3000 is fired by driving a firing slide 3010 distally through the advancement of a firing lever 3012. Distal movement of the firing slide 3010 causes a plurality of cam bars to engage camming surfaces that interact with a plurality of pushers to expel the plurality of surgical fasteners from the cartridge receiving half-section 3002. The surgical fasteners are positioned on either side of a track which guides a knife during longitudinal movement to thereby sever tissue along a cut-line.

Figure 50:
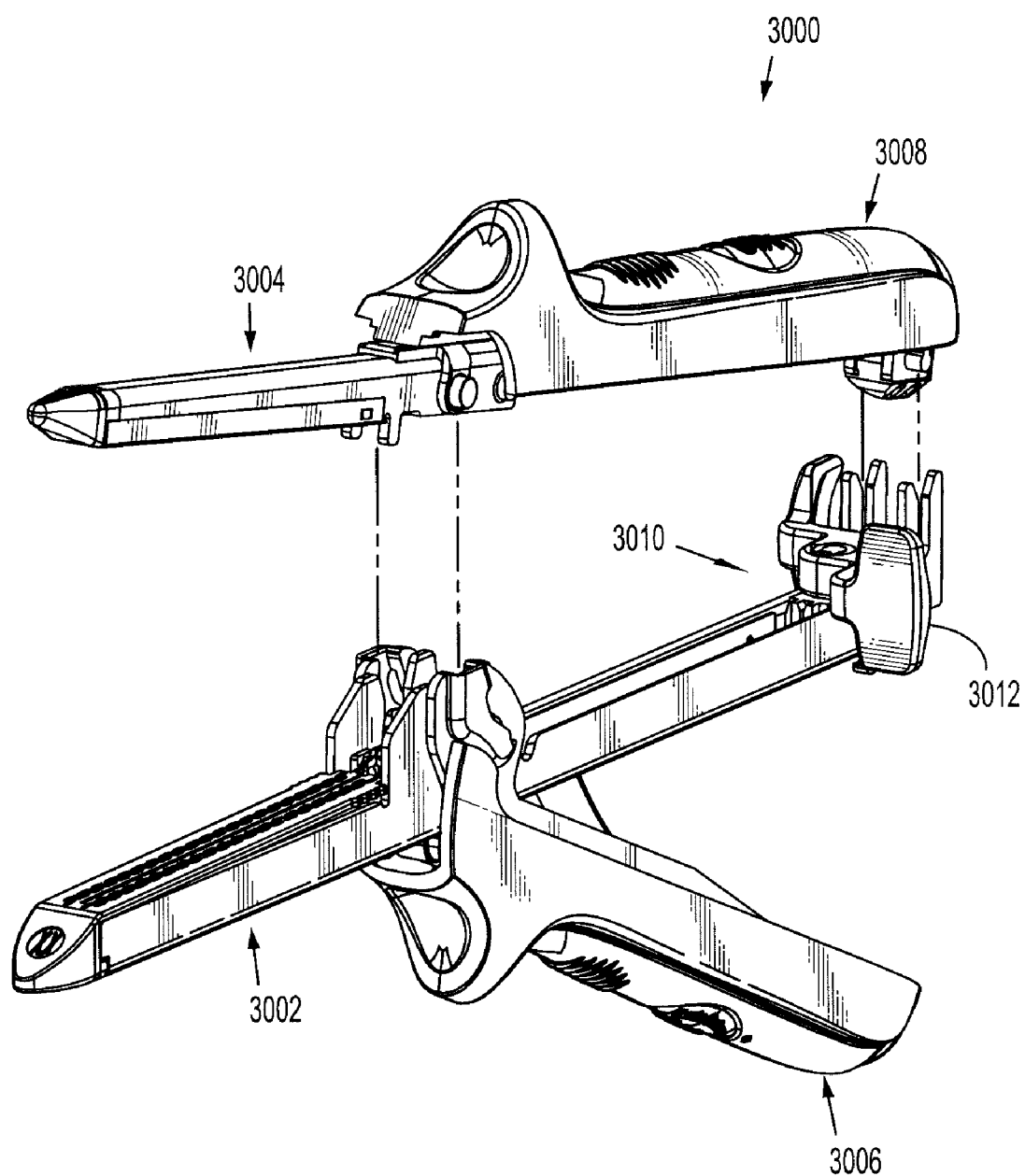
FIG. 50 illustrates a surgical fastener applying instrument for use with one embodiment of the presently disclosed introducer member.
Figure 51:
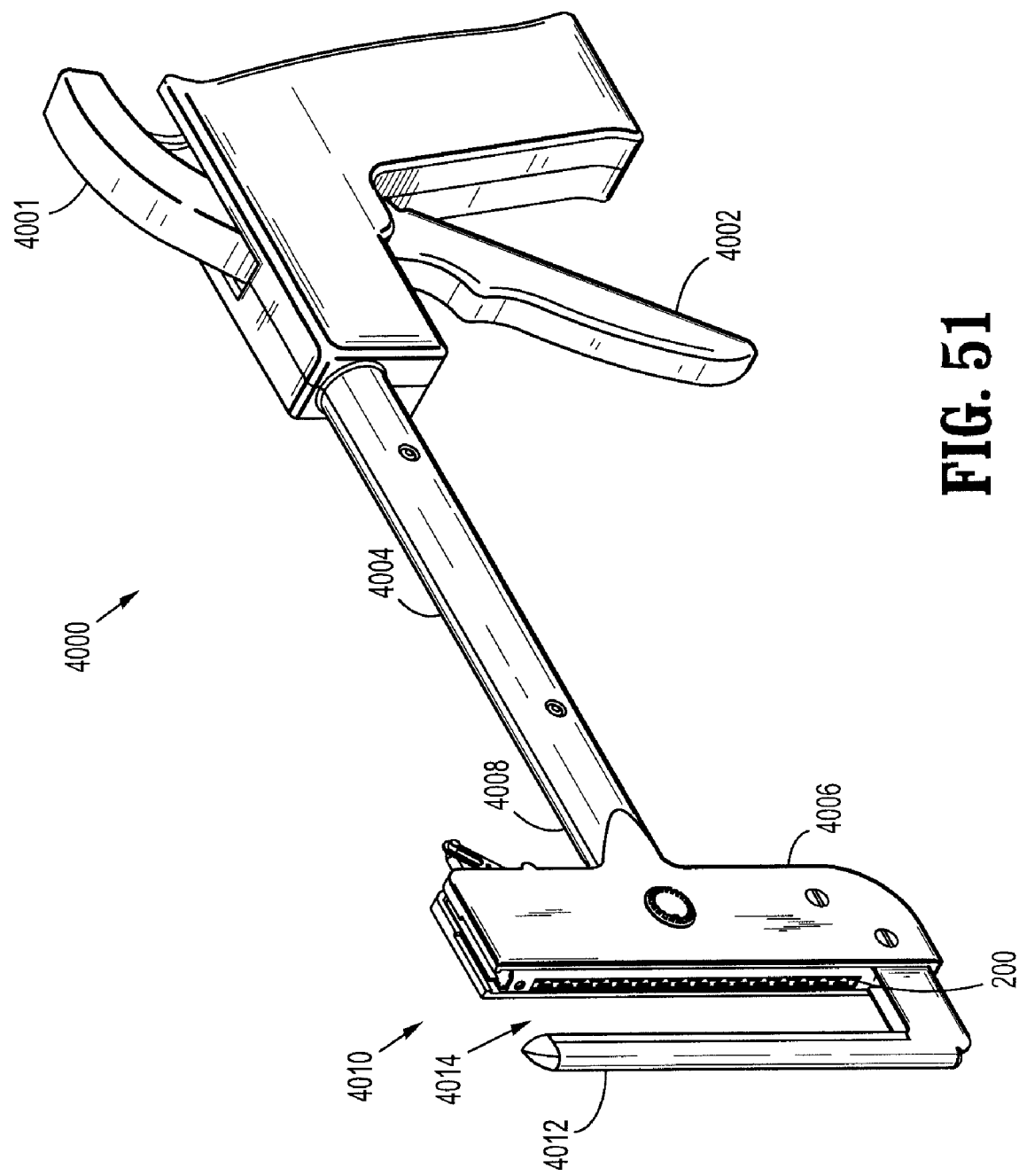
FIG. 51 illustrates a transverse anastomosis fastener applying instrument for use with another embodiment of the presently disclosed introducer member.

It is also envisioned that the presently disclosed introducer member may be adapted for use with a transverse anastomosis fastening instrument 4000 (FIG. 50), such as that disclosed in commonly owned U.S. Pat. No. 5,964,394, currently assigned to United States Surgical Corporation, the contents of which are hereby incorporated by reference herein in its entirety. The surgical fastener applying apparatus 4000 includes an approximation lever 4001, a movable handle 4002, an elongated portion 4004 that extends distally from the handle 4002, and an arm 4006 that extends from a distal end 4008 of the elongated portion 4004. The surgical fastener applying apparatus 4000 further includes a end effector 4010 that includes an anvil 4012 that is orthogonally affixed to the arm 4006, and a surgical fastener cartridge receiver 4014 that is operatively coupled to the distal end 4008 of the elongated portion 4004 for retention of the surgical fastener cartridge 200.

Prior to firing of the surgical fastener applying apparatus 4000, the approximation lever 4001 is actuated to distally advance a drive member that is operatively connected to the surgical fastener cartridge 200 to move the surgical fastener cartridge 200 towards the anvil 4012, which remains stationary, and capture tissue therebetween. Thereafter, the handle 4002 is moved to advance a pusher bar distally through the elongated portion 4004 to cause corresponding movement of a head portion included at the distal end of the pusher bar. The head portion includes a plurality of fingers extending distally therefrom that are configured and dimensioned to engage the cartridge assembly to thereby discharge the plurality of surgical fasteners retained therein. Upon discharge, the surgical fasteners are driven through the tissue and into the anvil 4012 for formation.

Additionally, it is envisioned that the presently disclosed introducer member may be adapted for use with any of the other surgical fastener applying apparatus discussed in commonly owned U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, the disclosures of which are hereby incorporated by reference herein in their entirety.

In certain embodiments of the present disclosure, it is envisioned that the disclosed surgical fastener applying apparatus may include a plurality of cam bars for interacting with the pushers to deploy the surgical fasteners. For example, the apparatus disclosed in commonly owned U.S. Pat. No. 5,318,221, the disclosure of which is hereby incorporated by reference herein in its entirety, includes a cam bar adapter that holds a plurality of cam bars and a knife, as well as a channel that is advanced through operation of the handle of the apparatus, which drives the cam bars and knife forward. To clamp the anvil and the surgical fastener cartridge together, the apparatus further includes a clamp tube that is movable to surround the proximal end of the anvil.

As another example, the apparatus disclosed in U.S. Pat. No. 5,782,396, the disclosure of which is hereby incorporated by reference herein in its entirety, includes an actuation sled and an elongated drive beam that is advanced distally through operation of the handle of the apparatus, driving the actuation sled forward. In this apparatus, the distal end of the drive beam engages the anvil and the channel that supports the surgical fastener cartridge as the drive beam travels distally to deploy the staples and clamp the anvil and surgical fastener cartridge together.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the invention is not to be limited by what has been particularly shown and described, except as indicated by the appended claims.

What is claimed is:

1. A surgical fastener applying apparatus, comprising:
   an elongate body portion having proximal and distal ends;
   an end effector positioned at the distal end of the elongate body portion and extending along a longitudinal axis, the end effector including a first jaw movably coupled to a second jaw such that target tissue is positionable therebetween, one of the first and second jaws terminating in a dissector tip; and
   an introducer member having proximal and distal ends, and being secured to the end effector such that the introducer member is movable relative to the end effector along the longitudinal axis between a retracted position and an advanced position.

2. The surgical fastener applying apparatus of claim 1, wherein the introducer member is secured to the first jaw such that the distal end of the introducer member is positioned proximally of a distal-most tip of the anvil component when the introducer member is in the retracted position, and the distal end of the introducer member is positioned distally of the distal-most tip of the anvil component when the introducer member is in the advanced position.

3. The surgical fastener applying apparatus of claim 2, wherein the first jaw includes a slot formed therein configured and dimensioned to accommodate the introducer member, the introducer member being movable within the slot during movement between the retracted position and the advanced position.

4. The surgical fastener applying apparatus of claim 3, wherein the first jaw includes an anvil component, and the second jaw includes a surgical fastener cartridge configured and dimensioned to retain a plurality of surgical fasteners therein.

5. The surgical fastener applying apparatus of claim 4, wherein the anvil component includes an anvil plate, and an anvil cover, the slot being formed in the anvil cover.

6. The surgical fastener applying apparatus of claim 1, wherein the introducer member includes a manual member configured and dimensioned for engagement by a user to facilitate manual repositioning of the introducer member between the retracted position and the advanced position.

7. The surgical fastener applying apparatus of claim 6, wherein the manual member extends outwardly from the introducer member.

8. The surgical fastener applying apparatus of claim 1, wherein the introducer member is at least partially formed from a flexible material.

9. A surgical fastener applying apparatus, comprising:
a handle assembly;
an elongate body portion extending distally from the handle assembly, the elongate body portion having proximal and distal ends;
an end effector positioned at the distal end of the elongate body portion and extending along a longitudinal axis, the end effector including an anvil component and a surgical fastener cartridge coupled together such that target tissue is positionable therebetween, the anvil component terminating in a dissector tip; and
an introducer member having proximal and distal ends, and being secured to the anvil component such that the introducer member is movable relative to the anvil component along the longitudinal axis between a retracted position and an advanced position.

10. The surgical fastener applying apparatus of claim 9, wherein the introducer member is secured to the anvil component such that the distal end of the introducer member is positioned proximally of a distal-most tip of the dissector tip when the introducer member is in the retracted position, and the distal end of the introducer member is positioned distally of the distal-most tip of the dissector tip when the introducer member is in the advanced position.

11. The surgical fastener applying apparatus of claim 10, wherein the anvil component includes an anvil plate, and an anvil cover, the anvil cover having a slot formed therein configured and dimensioned to accommodate the introducer member, the introducer member being movable within the slot during movement between the retracted position and the advanced position.

12. The surgical fastener applying apparatus of claim 9, wherein the introducer member is at least partially formed from a flexible material.

13. The surgical fastener applying apparatus of claim 9, wherein the handle assembly includes a stationary handle and a movable handle.

14. A method of applying a surgical fastener to tissue using a surgical fastener applying apparatus including an end effector having first and second jaws, and an introducer member secured to the end effector, the method comprising:
advancing the introducer member relative to the end effector along a longitudinal axis of the end effector such that a distal end of the introducer member is positioned distally of a distal-most tip of the end effector;
isolating target tissue via manipulation of the surgical fastener applying apparatus, whereby the introducer member separates the target tissue from collateral tissues adjacent the target tissue;
positioning the first and second jaws about the target tissue;
approximating the first and second jaws to secure the target tissue therebetween; and
firing the surgical fastener applying apparatus to eject the surgical fastener.

* * * * *